US012628802B2

(12) United States Patent
Yu et al.

(10) Patent No.: US 12,628,802 B2
(45) Date of Patent: May 19, 2026

(54) GENETICALLY MODIFIED RAT HAVING PKHD1L1 GENE WITH POINT MUTATION AND METHODS FOR ITS CONSTRUCTION, DETECTION AND USE

(71) Applicant: HUASHAN HOSPITAL AFFILIATED TO FUDAN UNIVERSITY, Shanghai (CN)

(72) Inventors: Peimin Yu, Shanghai (CN); Xiantao Li, Shanghai (CN); Yimin Sun, Shanghai (CN); Lan Xu, Shanghai (CN); Yue Wang, Shanghai (CN)

(73) Assignee: HUASHAN HOSPITAL AFFILIAED TO FUDAN UNIVERSITY, Shanghai (CN)

( * ) Notice: Subject to any disclaimer, the term of this patent is extended or adjusted under 35 U.S.C. 154(b) by 0 days.

(21) Appl. No.: 18/948,566

(22) Filed: Nov. 15, 2024

(65) Prior Publication Data

US 2025/0064034 A1     Feb. 27, 2025

Related U.S. Application Data

(63) Continuation of application No. PCT/CN2023/120325, filed on Sep. 21, 2023.

(30) Foreign Application Priority Data

Dec. 6, 2022    (CN) .......................... 202211558984.6
Jun. 28, 2023    (CN) .......................... 202310770803.4

(51) Int. Cl.
| | |
|---|---|
| *A01K 67/0278* | (2024.01) |
| *A61B 5/00* | (2006.01) |
| *A61B 5/383* | (2021.01) |
| *C12N 9/22* | (2006.01) |
| *C12N 15/11* | (2006.01) |
| *C12N 15/66* | (2006.01) |
| *C12Q 1/686* | (2018.01) |
| *C12Q 1/6888* | (2018.01) |

(52) U.S. Cl.
CPC .......... *A01K 67/0278* (2013.01); *A61B 5/383* (2021.01); *A61B 5/4094* (2013.01); *C12N 9/22* (2013.01); *C12N 15/111* (2013.01); *C12N 15/66* (2013.01); *C12Q 1/686* (2013.01); *C12Q 1/6888* (2013.01); *A01K 2227/105* (2013.01); *A01K 2267/0356* (2013.01); *C12N 2310/20* (2017.05); *C12Q 2600/124* (2013.01)

(58) Field of Classification Search
CPC .......... A01K 67/0278; A01K 2227/105; A01K 67/027
See application file for complete search history.

(56) References Cited

FOREIGN PATENT DOCUMENTS

| | | |
|---|---|---|
| CN | 101485917 A | 7/2009 |
| CN | 109820845 A | 5/2019 |
| CN | 111004818 A | 4/2020 |
| CN | 112168420 A | 1/2021 |
| CN | 113897399 A | 6/2022 |

OTHER PUBLICATIONS

NC_005106.4, Rat PKHD1L1 gene locus, available Jul. 1, 2014 (Year: 2014).*
Sequence alignment between NC_005106.4 and SEQ 5 (Year: 2025).*
NM_177531.5, Available from Aug. 15, 2017 (Year: 2017).*
NP_001030103.2 (Year: 2007).*
NP_803875.1 (Year: 2006).*
Sequence alignment between NC_005106.4 and SEQ 6 (Year: 2025).*
Yoshimi et al (ssODN-mediated knock-in with CRISPR-Cas for large genomic regions in zygotes. Nat. Commun. 7:10431 (2016) ( Year: 2016).*
International Search Report, International Appl. No. PCT/CN2023/ 120325, Dec. 1, 2023.
Written Opinion, International Appl. No. PCT/CN2023/120325, Dec. 1, 2023.

* cited by examiner

*Primary Examiner* — Emily A Cordas
*Assistant Examiner* — Matasha Dhar
(74) *Attorney, Agent, or Firm* — Central California IP Group, P.C.; Andrew D. Fortney

(57) ABSTRACT

A genetically-modified rat having a PKHD1L1 gene with a point or other mutation and a construction method thereof are disclosed. A CRISPR/Cas9 system knocks the PKHD1L1 gene into a rat source, and a codon changes from TTA to TCA to construct the mutant PKHD1L1 gene. The genetically-modified rat can be applied to epilepsy pathogenesis studies and design and testing of new anti-epileptic drugs. Methods for detecting abnormal cortical excitability and detecting an epileptic phenotype of an animal can use the genetically-modified rat. A somatosensory evoked potential is used to detect whether the genetically-modified rat has an abnormal cortical excitability phenotype, so as to confirm whether the rat can be a successful model for testing anti-epileptic drugs. The method can detect abnormal cortical excitability and verify the effectiveness of anti-epileptic drugs or treatments.

8 Claims, 12 Drawing Sheets

Specification includes a Sequence Listing.

Gene Type

A/T Type

A/A Type

Wild type allele

Targeting vector

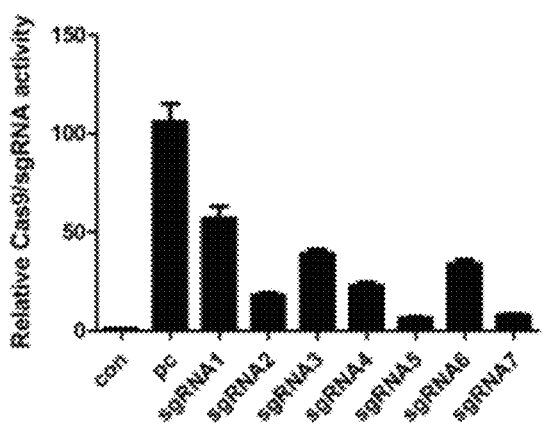
Fig. 5A                    Fig. 5B
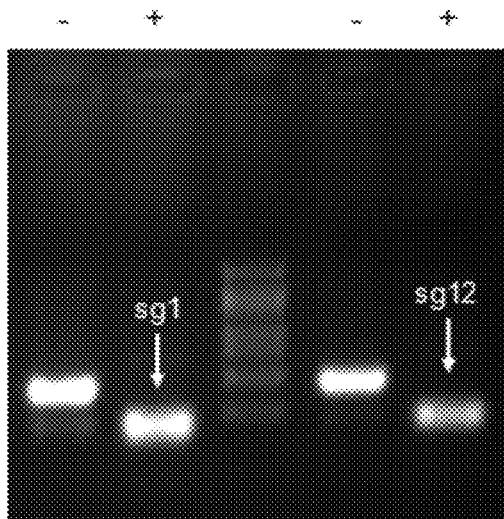
Fig. 6
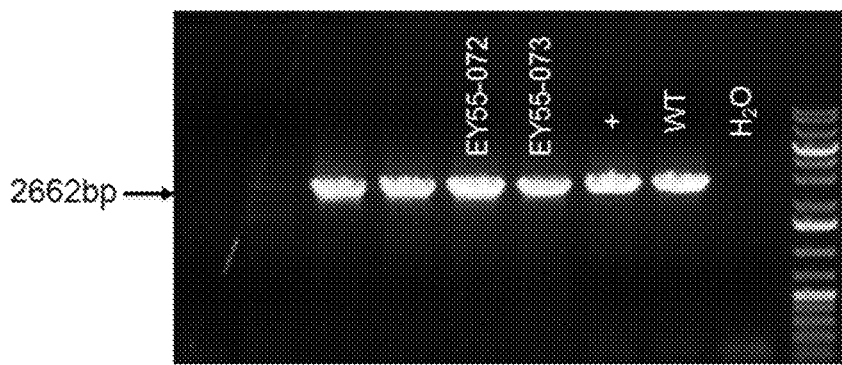
Fig. 7

First Dose PTZ (40mg/kg)
Seizure Occurrence

First Dose PTZ (40mg/kg)
Highest Seizure Score

5 Score Seizure PTZ dose

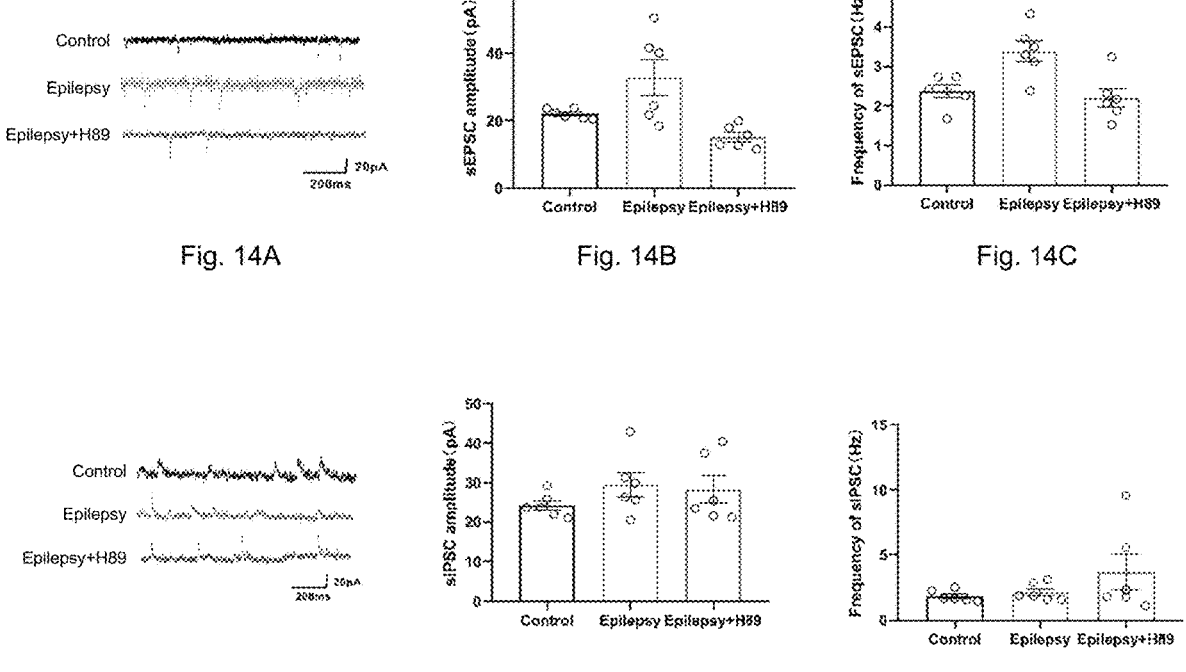
Fig. 14A                    Fig. 14B                    Fig. 14C
Fig. 14D                    Fig. 14E                    Fig. 14F

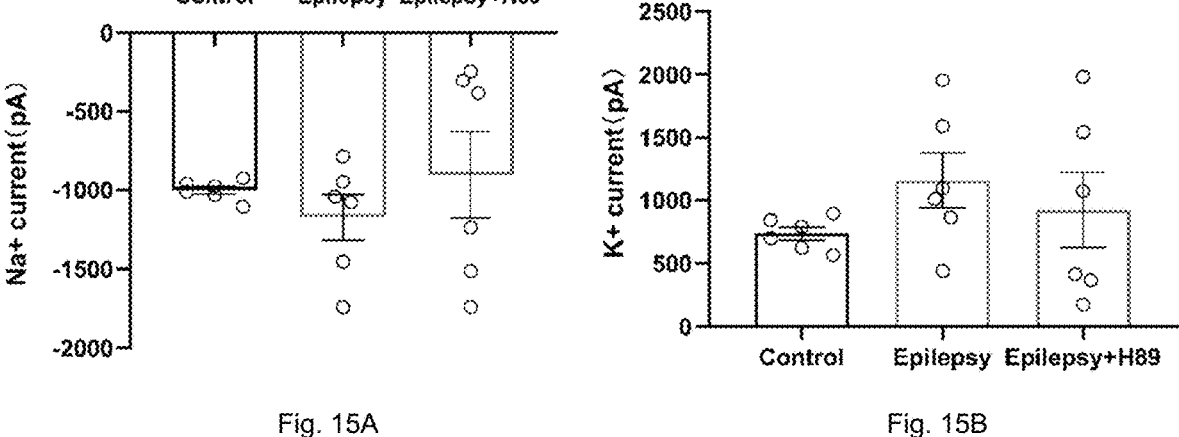
Fig. 15A                                        Fig. 15B

GENETICALLY MODIFIED RAT HAVING PKHD1L1 GENE WITH POINT MUTATION AND METHODS FOR ITS CONSTRUCTION, DETECTION AND USE

CROSS-REFERENCE TO RELATED APPLICATIONS

This application is a continuation of International Pat. Appl. No. PCT/CN2023/120325, filed Sep. 21, 2023, which claims the priority of the Chinese patent application with the title of "Construction and Application of a Point Mutation Rat Epilepsy Model," filed with the China National Intellectual Property Administration on Dec. 6, 2022, application Ser. No. 202211558984.6, and the Chinese patent application with the title of "A Method and Application for Identification of Cortical Excitability Abnormalities in an Animal Model of Epilepsy," filed with the China National Intellectual Property Administration on Jun. 28, 2023, application Ser. No. 202310770803.4, both of which are incorporated herein by reference as if fully set forth herein.

TECHNICAL FIELD

The contents of the electronic sequence listing (SHCH-2200251US 20240917.xml; Size: 32,127 bytes; and Date of Creation: Nov. 15, 2024) is incorporated herein by reference in its entirety.

BACKGROUND

Epilepsy is a serious chronic disease of the central nervous system, and is a temporary brain dysfunction caused by repeated attacks and highly synchronized abnormal discharge of brain neurons. It is clinically manifested by different disorders such as movement, sensation, consciousness, autonomic nerve and spirit, and is one of the more common diseases of the nervous system, affecting more than 65 million people. Disability, death and complications related to epilepsy have caused a heavy burden to patients and society. At present, little is known about the pathogenesis of epilepsy, and there is even significant heterogeneity in the pathogenesis considered by different scholars. Therefore, various animal models have been constructed to explain the pathogenesis of epilepsy. The animal models of epilepsy refer to specific species with an externally induced or inherited tendency to seizure. Therefore, in order to detect changes in electroencephalograms (EEGs), as well as behavioral characteristics in the state of epileptic seizures, a large number of epilepsy model studies have used inducible factors to keep epileptic seizures persistent. For example, one TLE animal model was constructed by intraperitoneally administering pilocarpine or pentylenetetrazole. Another animal model of TLE was established by injection of kainic acid into a lateral ventricle. However, the existing animal models of epilepsy cannot fully meet the clinical needs of epilepsy pathogenesis, pathophysiological process and treatment target screening. There are many kinds of animal models to explain the pathogenesis of epilepsy, so it is still unknown whether the constructed models can truly reflect the pathogenesis of epilepsy.

The detection of the constructed model is a necessary step, but there is no unified standard for detecting the successful construction of an animal epilepsy model in the existing data. For example, the common epilepsy model built with zebrafish needs to be detected by a zebrafish behavior meter, and the degree of epilepsy can be reflected according to the change of activity intensity of young zebrafish. In another example, in the Chinese patent CN201910244481.3 (entitled "A new method of drug-induced epilepsy model"), after drug induction, EEG detection of animal brainwaves, behavioral grading evaluation of epileptic rats, culture of primary hippocampal neurons in vitro, cell administration, and determination of the firing function of primary hippocampal neurons by a patch-clamp technique, it is necessary to determine whether the final rat model is epileptic.

It is known that an electrophysiological signal is the gold standard to evaluate the occurrence of epilepsy (or increased cortical excitability) and the effectiveness of drug intervention, but how to detect the corresponding animal model and/or its successful construction has become a technical problem to be solved.

SUMMARY

One purpose of the invention is to provide a genetically modified (e.g., point mutant) rat, useful as a model for epilepsy, and methods for the construction and use/applications thereof. The mutant rat has a phenotype including increased neuronal excitability, which can simulate the phenotype of familial cortical myoclonic tremor with epilepsy (FCMTE) and other epilepsy patients. The mutant rat can also be useful for studying or determining the pathogenesis of epilepsy and for designing and testing novel anti-epileptic drugs.

Another purpose of the invention is to provide a method of and use for identifying cortical excitability abnormalities (e.g., abnormal cortical excitability) in an animal model of epilepsy. To determine whether the genetically modified (e.g., transgenic and/or mutant) rat was successfully constructed, a method using somatosensory evoked potential (SEP) to detect a phenotype including abnormal cortical excitability was created. This method can be extended to determine whether other animal models of epilepsy are successfully constructed.

The invention provides a method for constructing a genetically-modified rat (e.g., a rat model having a PKHD1L1 gene with a point mutation therein), including the following steps: designing (and optionally making or synthesizing) single-guide RNA (sgRNA) using introns 22-23 and introns 24-25 of a PKHD1L1 gene as target sequences, annealing the sgRNA, ligating the annealed sgRNA into a plasmid vector with a T7 promoter, transcribing (e.g., the plasmid vector with the sgRNA therein) in vitro to obtain Cas9/sgRNA, injecting (e.g., microinjecting) the Cas9/sgRNA and a targeting vector into fertilized rat eggs, and placing the fertilized rat eggs with the Cas9/sgRNA and the targeting vector therein into a uterus of one or more pseudopregnant young rats (e.g., young rats with or exhibiting a false pregnancy). The $F_0$ generation rat (i.e., the first generation transgenic or mutant rat[s], obtained from a young rat implanted with the fertilized rat eggs) are chimeric, with a mutation (e.g., a point mutation) in the PKHD1L1 gene (e.g., the rat[s] have a PKHD1L1 gene point mutation chimeric). In the context of the present disclosure, a "PKHD1L1 gene" may refer to a gene that encodes a protein or polypeptide associated with a polycystic kidney and hepatic disease or functionally similar to such a protein or polypeptide (e.g., fibrocystin, fibrocystin-L), which may be autosomal recessive, and which may include a PKHD1 gene or a PKHD1L1 gene.

Preferably, the method includes amplifying introns 22-23 (or the corresponding target sequences) by a polymerase chain reaction (PCR) using primer pairs including PKHD1L1-5' MSD-F and PKHD1L1-5' MSD-R. The nucleotide sequence of PKHD1L1-5' MSD-F is shown in SEQ ID NO: 1, and the nucleotide sequence of PKHD1L1-5' MSD-R is shown as SEQ ID NO: 2. The method may further include amplifying introns 24-25 (or the corresponding target sequences) using primer pairs including PKHD1L1-3' MSD-F and PKHD1L1-3' MSD-R. The nucleotide sequence of PKHD1L1-3' MSD-F is shown in SEQ ID NO: 3, and the nucleotide sequence of PKHD1L1-3' MSD-R is shown in SEQ ID NO: 4.

Preferably, the PCR includes conditions of 94° C. for 5 min; 94° C. for 30 s, 62° C. for 30 s, 72° C. at 1 kb/min, a total of 30 cycles, and 72° C. for 10 min. For example, the PCR may comprise heating (e.g., the target sequences and, optionally, reagents and enzyme[s] for conducting PCR amplification) at 94° C. for 5 min, optionally heating (e.g., the target sequences and, optionally, the reagents and enzyme[s]) at 94° C. for another 30 seconds (herein after, the unit "seconds" may be abbreviated as "s"), annealing (e.g., the target sequences and, optionally, the reagents and enzyme[s]) at 62° C. for 30 s, and extending (e.g., the target sequences) at 72° C. at 1 kb/min; repeating the heating, annealing and extending steps up to a total of 30 cycles (e.g., 19-29 times); and optionally finally heating, annealing and/ or extending the PCR mixture at 72° C. for 10 min. The PCR amplification may produce the sgRNA or the target sequences in a quantity sufficient to connect (e.g., insert or splice) the same into the plasmid vector with the T7 promoter and isolate the plasmid vector with the T7 promoter and the target sequences therein.

Preferably, the sgRNA has a sequence as shown in (e.g., including or consisting of) SEQ ID NO: 5 and/or SEQ ID NO: 6.

Preferably, the plasmid vector includes a pCS-3G vector. The sgRNA may be ligated into the pCS-3G vector by annealing polymerization to form a connected product, and the connected product is transcribed in vitro to obtain the Cas9/sgRNA.

Preferably, the targeting vector has a nucleotide sequence including or consisting of SEQ ID NO: 27.

Preferably, the method further comprises, after obtaining the F_0 generation rats from at least one of the pseudopregnant young rats, identifying the rat(s) having the PKHD1L1 gene point mutation chimeric (e.g., the genetically modified or point mutant chimeric rat[s]) by PCR.

When identifying the genetically modified rat (e.g., the F_0 generation rat[s] having the PKHD1L1 gene point mutation chimeric) using PKHD1L1-L-GT-F and PKHD1L1-L-GT-R, a 2662 bp sequence may be amplified. The nucleotide sequence of PKHD1L1-L-GT-F is shown as SEQ ID NO: 7, and the nucleotide sequence of PKHD1L1-L-GT-R is shown as SEQ ID NO: 8.

When identifying the genetically modified rat (e.g., the F_0 generation rat[s] having the PKHD1L1 gene point mutation chimeric) using PKHD1L1-R-GT-F and PKHD1L1-R-GT-R, a 2697 bp sequence may be amplified. The nucleotide sequence of PKHD1L1-R-GT-F is shown as SEQ ID NO: 9, and the nucleotide sequence of PKHD1L1-R-GT-R is shown as SEQ ID NO: 10.

Preferably, the PCR conditions when identifying the genetically modified rat (e.g., having the PKHD1L1 gene point mutation chimeric) include pre-denaturing (e.g., the DNA or other polynucleic acid from the genetically modified rat) at 94° C. for 2 min, denaturing (e.g., the DNA or other polynucleic acid) at 98° C. for 10 s, annealing (e.g., the DNA or other polynucleic acid with one or more reagents and/or enzymes for the PCR) at 67° C. for 30 s, extending (e.g., the PKHD1L1 gene with the mutation therein from the genetically modified rat) at 68° C. at 1 kb/min, repeating the denaturing, annealing, and extending for up to a total of 15 cycles (e.g., repeating 9-14 times), annealing (e.g., the PKHD1L1 gene with the mutation therein with one or more of the reagents and/or enzymes for the PCR) at a temperature of −0.7° C. per cycle, denaturing again (e.g., the polynucleic acid containing the PKHD1L1 gene with the mutation therein) at 98° C. for 10 s, annealing again (e.g., the polynucleic acid containing the mutant PKHD1L1 gene with reagent[s] and/or enzyme[s] for the PCR) at 57° C. for 30 s, extending again (e.g., the polynucleic acid containing the mutant PKHD1L1 gene) at 68° C. at 1 kb/min, repeating the denaturing again, annealing again, and extending again for up to a total of 25 cycles (e.g., 14-24 times), and finally extending the polynucleic acid containing the mutant PKHD1L1 gene at 68° C. for 10 min.

The invention also provides a method for constructing a stable genetically-modified rat (e.g., having a PKHD1L1 gene with a point mutation therein), including mating the genetically-modified (e.g., F_0 generation) rat(s) with one or more wild-type rats (e.g., to obtain one or more F_1 generation rats), wherein the stable genetically-modified rat(s) (e.g., the F_1 generation rat[s] having the PKHD1L1 with the mutation therein) are heterozygous (e.g., a heterozygote of the F_1 generation). The heterozygote (e.g., the heterozygous stable genetically-modified rat) may be identified by genotype identification.

The invention also provides an application of a method of screening and/or developing epilepsy drugs using the genetically modified rat(s) (e.g., obtained by the method of constructing a genetically modified rat or the PKHD1L1 gene point mutation rat model) or the stable genetically modified rat(s) (e.g., obtained by the method for constructing a stable genetically modified rat or the stable genetic PKHD1L1 gene point mutation rat model).

The invention provides an application of a method for determining the phenotype of a possibly epileptic animal or an epileptic animal model (e.g., a genetically modified rat having a recombinant PKHD1L1 gene or the point-mutated PKHD1L1 gene) by detecting abnormal cortical excitability.

Preferably, detecting abnormal cortical excitability includes determining or detecting somatosensory evoked potentials (e.g., in the epileptic animal).

The invention also provides a method of detecting a phenotype of an epileptic animal model or possibly epileptic animal, which comprises the following steps: fixing the head and limbs of the animal or model in a prone position, electrically stimulating a posterior tibial nerve (e.g., in the ankle of the right or left hind limb of the epileptic animal) by or through the skin, inserting or placing a recording needle and/or electrode into a subcutaneous region of the cranial roof (e.g. of the possibly epileptic animal or model, optionally in the Cz region of the cranial roof), and inserting or placing a reference needle and/or electrode into the nose (e.g. of the epileptic animal, subcutaneously) or a subcutaneous area above the nose.

The method of detecting the phenotypic of the epileptic animal may further comprise extracting a signal (e.g., from the recording needle and/or electrode), filtering and amplifying the signal, measuring a peak latency (e.g., using an input system) according to a somatosensory evoked potential (e.g., output in the extracted signal), evaluating a cortical excitability (e.g., based on the peak latency and/or the somatosensory evoked potential), and determining whether the animal is epileptic according to the cortical excitability.

Preferably, the posterior tibial nerve is electrically stimulated using a constant pressure square wave with a wave or pulse width of 0.1 ms and/or a frequency of 3 Hz. The constant pressure square wave has an intensity (e.g., power or strength) sufficient to cause the back toe (e.g., of the animal) to move or contract (e.g., to cause back toe micro-movement). A (further) subcutaneous needle in the back (e.g., of the animal) may be grounded.

Preferably, the method further comprises inputting the extracted signal (after filtering and amplification) into a computer or computer operating system for analysis (e.g., by determining an average superposition, for example with 1024 superposition times and an analysis duration of 56 ms). Finally, the method may further comprise displaying (and optionally printing) graphics including a pattern of the somosensory evoked potential. The peak latency may be measured using this somosensory evoked potential pattern.

Preferably, the epileptic animal includes a genetically modified epileptic rat or a genetically modified epileptic mouse.

Beneficial effects of the invention include preliminary confirmation that the heterozygous mutation c.2602A>T in exon23 of the PKHD1L1 gene is a pathogenic mutation of the family by a pathogenicity study of a family with familial adult myoclonic epilepsy (see FIG. 17). The invention uses a CRISPR/Cas9 system to modify a PKHD1L1 gene to change a TTA sequence or codon to a TCA sequence or codon (e.g., knock in the P.L867S mutation in the rat PKHD1L1 gene), so as to construct a PKHD1L1 point mutation in a genetically modified animal. Three male PKHD1L1 point-mutated heterozygous (PKHD1L1+/−) rats were observed for 5 consecutive days, and no spontaneous epilepsy was observed. However, PKHD1L1+/− rats showed a phenotype of increased neuronal excitability, and a significantly lower threshold concentration of intraperitoneally injected pentylenetetrazole (PTZ) that induces epileptic seizure (e.g., in the PKHD1L1+/− rats) than in wild-type rats, and the resting potential of brain electrophysiology of the PKHD1L1+/− rats was significantly lower than that of wild-type rats, enabling simulation of a FCMTE or other phenotype that may be characteristic of epileptic patients. The genetically-modified rat is useful for determining the pathogenesis of epilepsy, the design and testing of novel antiepileptic drugs, and various other research scenarios.

The invention provides a method for detecting abnormal cortical excitability to determine the phenotype of an epileptic or potentially epileptic animal. The method uses SEP to detect whether the constructed animal has an abnormal cortical excitability phenotype, so as to judge whether the construction is successful. The detection method of the invention can detect cortical excitability in rats or mice, and the detected value (e.g., of cortical excitability) can be used as an evaluation index for the efficacy of drugs that inhibit cortical excitability.

BRIEF DESCRIPTION OF THE DRAWINGS

FIGS. 5A-B are graphs showing the activity detection results of various sgRNA sequences in accordance with the present invention.

FIG. 6 is a reproduction of a Southern blot showing the results of RNA electrophoresis at 65° C. for 5 min, in which sg1 refers to PKHD1L1-sgRNA1, and sg2 refers to PKHD1L1-sgRNA12;

FIG. 7 is a reproduction of a Southern blot showing the results of $F_0$-generation identification by PCR using PKHD1L1-L-GT-F/PKHD1L1-L-GT-R in accordance with the present invention.

FIGS. 14A-F are waveforms (FIGS. 14A and 14D) and graphs (FIGS. 14B-C and 14E-F) showing the effect of H89 on sEPSC/sIPSC measurements of cortical pyramidal neurons, in which FIG. 14A shows sEPSC currents of pyramidal neurons in groups of control, epileptic and treated rats, FIG. 14B shows the sEPSC amplitudes in pyramidal neurons in the rats, FIG. 14C shows the sEPSC frequencies in pyramidal neurons in the rats, FIG. 14D shows sIPSC currents in pyramidal neurons of each group of rats; FIG. 14E shows sIPSC amplitudes in the pyramidal neurons in the rats; and FIG. 14F shows sIPSC frequencies in the pyramidal neurons in the rats (3 rats in each group and 6 cells in each group, * refers to P<0.05, and ** refers to P<0.01).

FIGS. 15A-B are graphs showing the effect of H89 on the Na+ and K+ currents in the cerebral cortex of the control, epileptic and treated groups of rats, wherein FIG. 15A shows the Na+ currents in the pyramidal neurons of the rats, and FIG. 15B shows the K+ currents in the pyramidal neurons of the rats (3 rats in each group, 6 cells in each group, P<0.05).

FIG. 16C is a graph showing the action potential threshold of the pyramidal neurons in each group of rats, FIG. 16D is a graph showing the positive post-potential recovery of the action potential in each group of rats, FIG. 16E is a graph showing the half-duration of the action potential in each group of rats, and FIG. 16F is a graph showing the peak action potential in each group of rats (3 rats per group, 6 cells in each group, and * refers to P<0.05).

DETAILED DESCRIPTION OF EMBODIMENTS

The invention concerns a method for constructing a genetically-modified rat having a PKHD1L1 gene with a mutation (e.g., a point mutation) therein, including the following steps: designing single-guide RNA (sgRNA) using introns 22-23 and introns 24-25 of a PKHD1L1 gene as target sequences, annealing the sgRNA, ligating the annealed sgRNA to a plasmid vector with a T7 promoter, and transcribing the plasmid vector in vitro to obtain Cas9/sgRNA. The Cas9/sgRNA and a targeting vector are injected into fertilized rat eggs to obtain gene-edited fertilized eggs, and the gene-edited fertilized eggs are placed or inserted into a uterus of one or more pseudopregnant young rats (e.g., with false pregnancy) to obtain $F_0$ generation, chimeric rats with the mutant PKHD1L1 therein.

Figure 17:
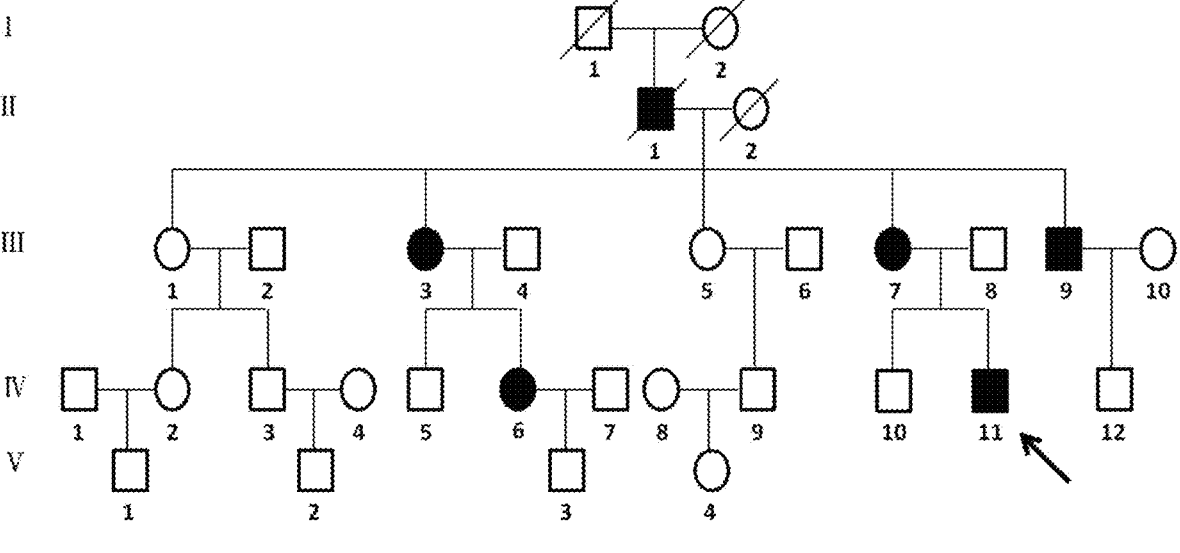
FIG. 17 is a diagram of an exemplary family with a history of familial adult myoclonic epilepsy.

The PKHD1L1 gene in the invention is preferably selected from a family with a history of familial adult myoclonic epilepsy. A family diagram showing such a family is shown in FIG. 17. The family has a total of 30 people in five generations and 6 patients with familial adult myoclonic epilepsy (identified in black), which conforms to the characteristics of autosomal dominant inheritance. All patients had myoclonic seizures with or without generalized tonic-clonic seizures and subtle tremors at the distal extremity. The onset of seizures was adult. Electroencephalographic examination (EEG) indicated bilateral symmetric spinoid-slow wave release, and evoked potential testing showed positive giant potential(s) and C-reflex. Anti-epileptic drug treatment effectively controlled the seizures, and the disease course was benign. All members of the family were effectively diagnosed and their clinical phenotypes were consistent. By whole genome exon sequencing combined with linkage analysis, it was found that 5 patients (1 of the 6 patients had died, as indicated by the slash through the black square in FIG. 17) had heterozygous mutations of the PKHD1L1 gene exon 23: c.2602A>T, and 11 family controls were homozygous with co-segregation.

Figure 1:
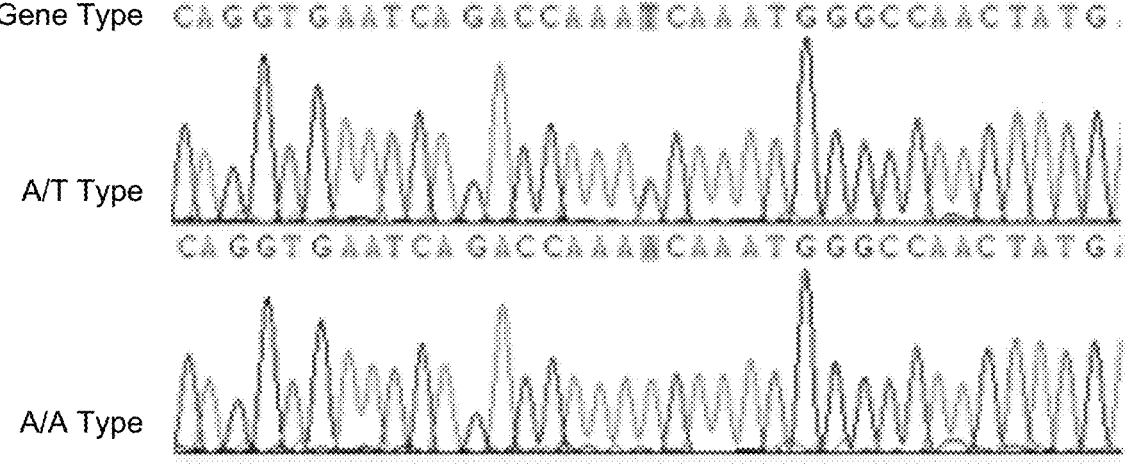
FIG. 1 shows the sequence of an exemplary PKDH1L1 gene mutation.

The PKHD1L1 gene was further screened in 246 cases (e.g., persons) from a normal population, matched by age, sex, region and ethnicity, and did not find the mutation in the normal population. Therefore, the heterozygous mutation of the PKHD1L1 gene exon 23: c.2602A>T (see FIG. 1) was preliminarily confirmed as a pathogenic mutation in the family in FIG. 17.

Figure 2:
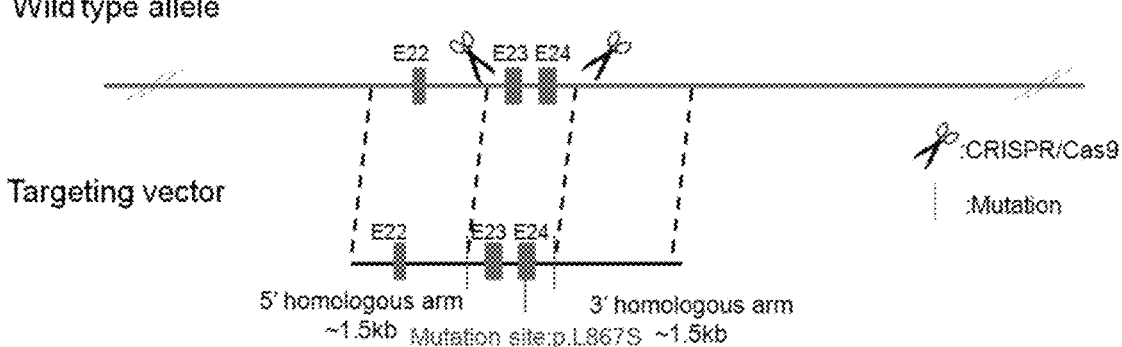
FIG. 2 is a diagram showing an exemplary construction strategy for a targeting vector useful in the present invention.

The PKHD1L1 gene that encodes the polycystic kidney and hepatic disease 1-like protein I is on the positive chain of chromosome 7, and has a total length of about 172.46 kb. The Gene ID of this gene in *Rattus norvegicus* (Norway rats) is 314917 In one example, a PKHD1L1-201 transcript (ENSRNOT00000005958.7, NM_001034931; referred to hereinafter "the example PKHD1L1 gene") was used to conduct a point mutation study in rats; Specifically, amino acid Leu at 867 of the example PKHD1L1 gene was mutated to Ser by a CRISPR/Cas9 system, the corresponding base was changed from TTA to TCA, and the sgRNA was designed using intron(s) 22-23 and intron(s) 24-25 (FIG. 2).

In one embodiment, in order to ensure the efficiency of the designed Cas9/sgRNA, PCR amplification and sequencing verification was performed on the single-stranded DNA (SD) rat target site sequence to ensure that the sgRNA recognition sequence is completely consistent with the SD rat DNA sequence. When the primers included PKHD1L1-5' MSD-F (SEQ ID NO: 1) and PKHD1L1-5' MSD-R (SEQ ID NO: 2), the amplified product has a length of 754 bp. When the primers included PKHD1L1-3' MSD-F (SEQ ID NO: 3) and PKHD1L1-3' MSD-R (SEQ ID NO: 4), the amplification product has a length of 569 bp. The PCR amplification procedure and conditions preferably include a temperature of 94° C. for 5 min; a temperature of 94° C. for another 30 s, a temperature of 62° C. for 30 s, a temperature of 72° C. at 1 kb/min, carried out for 30 cycles; and a temperature of 72° C. for 10 min. The PCR products were sequenced, and the results showed that the SD rat target sequence was completely consistent with the sequence obtained from Genebank and Ensembl, and are suitable for point mutated sgRNA target genes.

TABLE 1

Primers for amplification of rat target sequences by PCR

| Primer | Sequence (5'-3') | SEQ ID NO | Tm (° C.) | Prod. size (bp) |
|---|---|---|---|---|
| PKHD1L1-5' MSD-F | GCATCAAGCTTGGTACCGATAAT CACAAGACACAATAGACGCAGA | 1 | 61 | 754 |
| PKHD1L1-5' MSD-R | ACTTAATCGTGGAGGATGATCTT GCTTCACAAACAAAGGGACCTG | 2 | 63 | |
| PKHD1L1-3' MSD-F | GCATCAAGCTTGGTACCGATGAC AGAAGCAAAGCCAGAGAATAAA | 3 | 60 | 569 |
| PKHD1L1-3' MSD-R | ACTTAATCGTGGAGGATGATGAA GTTTACATAACTCAAGCAGTCCA | 4 | 60 | |

Two sgRNAs were designed and made based on the target gene(s), and the sgRNAs are specifically PKHD1L1-sgRNA1 (SEQ ID NO: 5) and PKHD1L1-sgRNA12 (SEQ ID NO: 6; see Table 2). The sgRNA(s) are optimally connected to a pCS-3G carrier (shown in FIG. 3) by annealing polymerization, and the connected product is converted into a sample for sequencing verification (e.g., Cas9/sgRNA that can be microinjected). The annealing polymerization preferably includes annealing at 65° C. for 5 min.

TABLE 2 sgRNA sequence

| sgRNA | GuideRNA sequence | SEQ ID NO |
|---|---|---|
| PKHD1L1-sgRNA1 | GGTAGGCTAGACTTTAA | 5 |
| PKHD1L1-sgRNA2 | GGCCTTCGTATTAGCTATA | 11 |
| PKHD1L1-sgRNA3 | GGAATCCCTATAGCTAATACGA | 12 |
| PKHD1L1-sgRNA4 | GGCTACTATGTTAAATATG | 13 |
| PKHD1L1-sgRNA5 | GGAGTCTTAAAGTGAACC | 14 |
| PKHD1L1-sgRNA6 | GGGAAGTTAAGAAACACAAT | 15 |
| PKHD1L1-sgRNA7 | GGCACCTGTGGGCATGTGTAGA | 16 |
| PKHD1L1-sgRNA8 | GGTCACCCTTAAGCCCCCAAAA | 17 |
| PKHD1L1-sgRNA9 | GGTCTACATGTATGTCACCACC | 18 |
| PKHD1L1-sgRNA10 | GGTTAATTTAGTCATGTATA | 19 |
| PKHD1L1-sgRNA11 | GGTCAAATAACTAGAACTGC | 20 |

TABLE 2-continued sgRNA sequence

| sgRNA | GuideRNA sequence | SEQ ID NO |
|---|---|---|
| PKHD1L1-sgRNA12 | GGAAAGTTGAGTGTTCCA | 6 |
| PKHD1L1-sgRNA13 | GGAAGTTATTTGTTATGAA | 21 |
| PKHD1L1-sgRNA14 | GGAAATCTGGGTCCTTAGAA | 22 |

Figure 4:
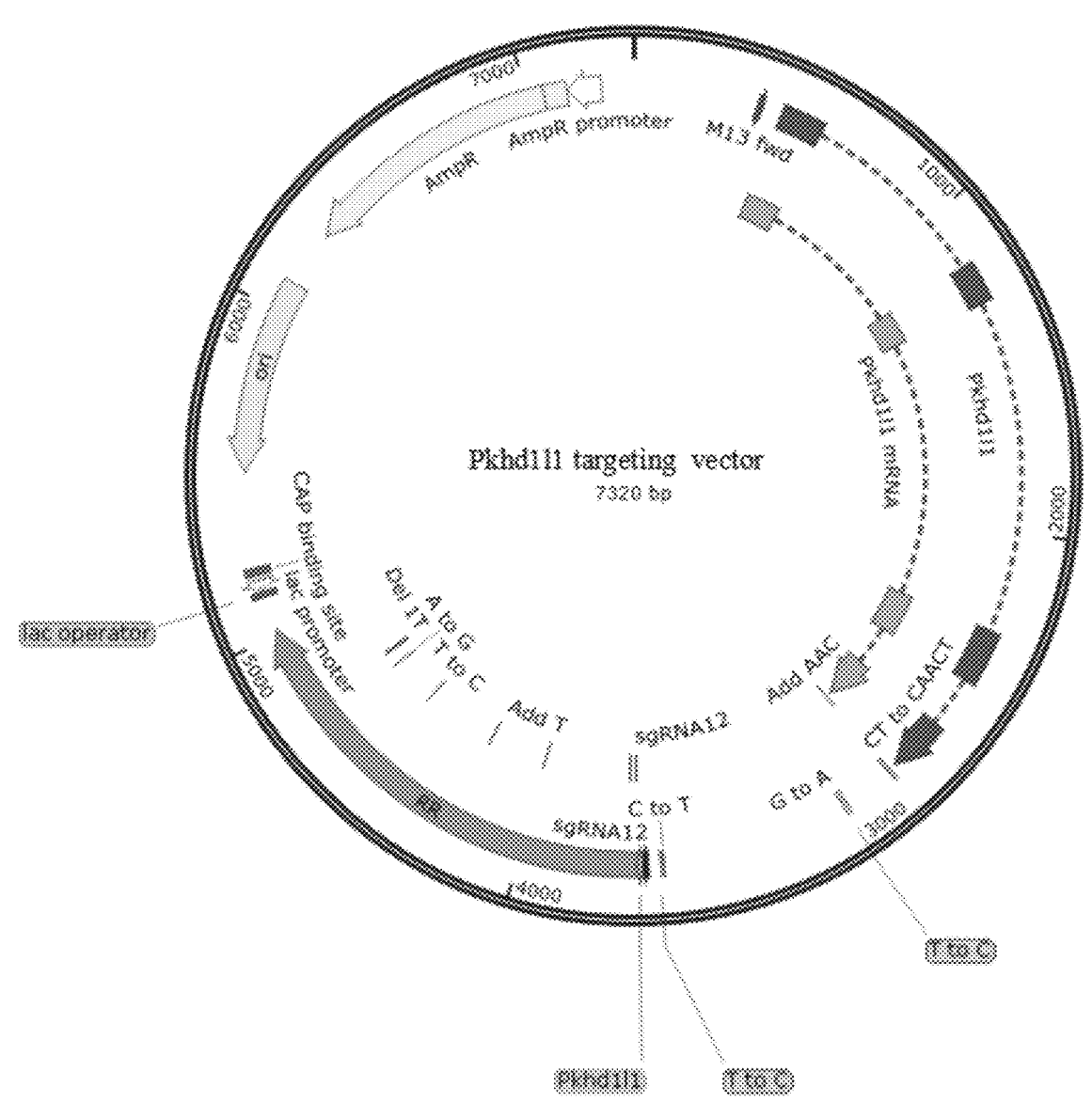
FIG. 4 shows the map of the targeting vector, created with SnapGene®.

The plasmid profile of the targeting vector for microinjection is shown in FIG. 4, and the nucleotide sequence of the targeting vector is shown in SEQ ID NO: 27.

Cas9/sgRNA and the targeting vector were microinjected into fertilized eggs of rats, and the $F_0$ rats were born after the injection (and implantation into young female rats with false pregnancy). The $F_0$ rats obtained were chimeras due to the rapid cleavage rate of the embryos in the early stage, and the chimeric rats were also identified by PCR after the $F_0$ generation. Chimeric rats are positive for both PKHD1L1-L-GT-F/PKHD1L1-L-GT-R (2662 bp) and PKHD1L1-R-GT-F/PKHD1L1-R-GT-R (2697 bp).

Preferably, PCR identification uses a Touchdown mode, and constructs the reaction system according to the instruction manual for KOD-FX® enzyme (available from Toyobo Co., Ltd., Osaka, Japan). The PCR identification procedure preferably includes: pre-denaturing at 94° C. for 2 min; denaturing at 98° C. for 10 s, annealing at 67° C. for 30 extending at 68° C. at 1 kb/min, and repeating the denaturing, annealing, and extending steps for a total of 15 cycles, annealing at a temperature of –0.7° C. per cycle; a second denaturing at 98° C. for 10 s, a second annealing at 57° C. for 30 s, a second extending at 68° C. at 1 kb/min, and repeating the second denaturing, annealing, and extending steps for a total of 25 cycles; and finally extending at 68° C. for 10 min:

TABLE 3

Primers for identification of
point mutation chimera

| Primer | Sequence (5'-3') | SEQ ID NO | Tm (° C.) | Product size (bp) |
|---|---|---|---|---|
| PKHD1L1-L-GT-F | tgcagatgttgtgagaaaagcaagaca | 7 | 60 | Mut: 2662 |
| PKHD1L1-L-GT-R | ccagtcttgatgttttatagatacttcccc | 8 | 59 | WT: 2650 |
| PKHD1L1-R-GT-F | tccaatccatttatgtggatgccgtgt | 9 | 62 | Mut: 2697 |
| PKHD1L1-R-GT-R | aggatgcttgaatctttcttctaagggg | 10 | 60 | WT: 2680 |

The invention also concerns a method for constructing a stable genetically modified rat with a point mutation in a PKHD1L1 gene, including the following steps: mating an $F_0$ generation chimeric rat with the point mutation (which may be obtained by the present method of constructing the $F_0$ generation chimeric rat) with a wild-type rat to produce an $F_1$ generation including the stable genetically modified rat with the point mutation in the PKHD1L1 gene. The $F_1$ generation rat with the PKHD1L1 gene point mutation is genetically stable and heterozygous.

In the present invention, the $F_0$ generation genotype-positive rat is selected to mate with one or more wild-type rats to obtain the $F_1$ generation rat with a stable genotype. The genotype of the $F_1$ generation rats is identified by PCR, Southern blot analysis and sequencing, in which the PCR for identification is the same or substantially the same as that for constructing and/or determining the $F_0$ generation, and it will not be repeated here. EcoRV and Spel were used as restriction enzyme sites for Southern blot analysis. Correct recombination was determined and/or detected using 3' Probe-A. When recombination is correct, two bands, wild-type and mutant type, appear (e.g., in the Southern blot). Random insertion was determined and/or detected using LR Probe-A. When no random insertion is detected, two bands, wild-type and mutant type, appear (e.g., in the Southern blot).

TABLE 4

Primer information of 3' Probe-A
and LR Probe-A

| Primer | Sequence (5'-3') | Product size (bp) | Tm (° C.) | SEQ ID NO |
|---|---|---|---|---|
| PKHD1L1-LR-Probe-A-F | aggatctctggccaacttcattgg | 470 | 60 | 23 |
| PKHD1L1-LR-Probe-A-R | ttctgtttctaatgttagtggaaatgc | | 55 | 24 |
| PKHD1L1-3'Probe-A-F | ccagtccccagaacaattggctaga | 546 | 61 | 25 |
| PKHD1L1-3'Probe-A-R | actgtgtggaggcaaagaagcatga | | 61 | 26 |

For $F_1$ and successive generations with point mutations, heterozygous and homozygous genotypes can also be detected by PCR validation and sequencing. The primers used for this detection include PKHD1L1-R-GT-F and PKHD1L1-L-GT-R, and the optimized conditions include a first stage at a temperature of 94° C. for 5 min, a cycling stage including a temperature of 94° C. for 30 s, a temperature of 62° C. for 30 s, a temperature of 72° C. at 1 kb/min, and a total of 30 cycles; and a final stage at a temperature of 72° C. for 10 min. Since the mutated and the wild-type sequences are both 625 bp, the homozygous, heterozygous and wild-type genotypes are confirmed by sequencing.

The invention also concerns methods of screening and/or developing epilepsy drugs, using a genetically modified rat having a PKHD1L1 gene with a point mutation therein or a stable genetically modified rat with the point mutation in the PKHD1L1 gene. The (stable) genetically modified rat may be obtained by one or more of the present construction methods.

The invention also provides a method of or application for detecting abnormal cortical excitability and/or detecting or determining a phenotype of an epileptic or possibly epileptic animal.

The method of detecting abnormal cortical excitability preferably includes determining (e.g., testing or obtaining) a somatosensory evoked potential (SEP) in the animal. There is no special limitation on the specific construction method or animal, although the animal is preferably a rat, mouse or zebrafish. A genetically-modified rat is an example and/or embodiment of the invention, but the invention is not limited to genetically-modified rats.

A mutation in the PKHD1L1 gene exon 23: c.2602A>T (which may be heterozygous) was confirmed as a pathogenic mutation in the family shown in FIG. 17 through a pathogenicity study of familial adult myoclonic epilepsy (FAME) in the family, and in one example, a CRISPR/Cas9 system was used to knock in the P.L867S mutation into the PKHD1L1 gene to change the corresponding codon from TTA to TCA, resulting in the construction of a PKHD1L1 point-mutant rat. An electrophysiological examination of the epileptic seizure patients in the family in FIG. 17 found increased cortical excitability (e.g., relative to a reference standard, an average for patients without epileptic seizures, or family members who do not experience epileptic seizures), and the seizures were effectively controlled by antiepileptic drug treatment. At the same time, the genetically modified rats having or expressing the mutant PKHD1L1 gene constructed in accordance with the invention showed significantly shorter incubation periods and increased SEP amplitudes, compared with wild-type rats with matching body weight, suggesting that the cortical excitability of PKHD1L1+/− rats was significantly higher than that of wild-type rats. This study further verified the increased cortical excitability of PKHD1L1+/− rats, which can better simulate the FAME phenotype and phenotypes of other epilepsy patients, and can be further applied to research into the pathogenesis of epilepsy and the design and testing of new anti-epileptic drugs.

The invention concerns a method for detecting a phenotype in an epileptic or possibly epileptic animal (e.g., an epileptic animal model), which comprises the following steps: fixing the head and limbs of the animal in a prone position, electrically stimulating the posterior tibial nerve of the ankle of a hind limb (e.g., the right hind limb) through the skin, subcutaneously placing a recording needle and/or electrode into the Cz region of the cranial roof, and subcutaneously placing a reference needle and/or electrode into an area above the nose (e.g., the bridge of the nose, the forehead, etc.).

The method for detecting a phenotype in an epileptic or possibly epileptic animal may further comprise extracting a signal (e.g., from the recording needle and/or electrode). After the extracted signal is filtered and amplified, an input system measures the peak latency according to one or more somatosensory evoked potentials (e.g., in or derived from the signal), evaluates a cortical excitability (e.g., based on the somatosensory evoked potential[s]), and determines whether the animal is epileptic according to the cortical excitability (or a level or value thereof).

Electrically stimulating the posterior tibial nerve may include transmitting a constant pressure square wave with a pulse or wave width of 0.1 ms and a frequency of 3 Hz (e.g., to the nerve). The intensity of the square wave may be sufficient to cause movement (e.g., micro-movement) in the back toe. Electrically stimulating the posterior tibial nerve may further include subcutaneously placing a needle in the back of the animal, and the needle may be grounded. The method for detecting a phenotype in an animal optimally filters and amplifies the extracted signal, and inputs it into a computer operating system for determining an average superposition (e.g., of the extracted signal). The average superposition may be determined from 1024 instances (e.g., superpositions), the analysis time may be 56 ms, and the computer operation system may be configured to display and print a pattern of somosensory evoked potentials to determine or measure a peak latency (e.g., of the somosensory evoked potentials, the pattern thereof, the average superposition, etc.).

In order to further illustrate the invention, the construction of a genetically-modified, mutant rat as a model for epilepsy and an application thereof are described in detail in combination with the accompanying drawings and below examples, but the invention is not limited to the drawings or examples.

Example 1: Screening for Disease-Causing Mutated Genes

In the family shown in FIG. 17 (Family 1), there are 30 people in five generations, of whom 6 had the disease (e.g., epilepsy), all 6 of which were consistent with autosomal dominant inheritance. All 6 patients had myoclonic seizures with or without generalized tonic-clonic seizures, and with or without subtle tremors at the distal extremity. The onset of seizures was adult, and electrophysiological examination showed increased cortical excitability. The seizures were effectively controlled by anti-epileptic drug treatment, and the course of the disease was benign. All patients in Family 1 were diagnosed clearly, and their clinical phenotypes were consistent. Whole genome exon sequencing combined with linkage analysis showed that 5 patients (1 of the 6 patients had died) had heterozygous mutations in PKHD1L1 gene exon 23: c.2602A>T, and 11 controls were homozygous with co-segregation.

The PKHD1L1 gene was screened in 246 normal people matched by age, sex, region, and ethnicity, and the mutation site could not be found in the normal population, so it was preliminarily confirmed by genetics that this site in PKHD1L1 was a pathogenic mutation in this family.

TABLE 5

| | | | | | | | | | | |
|---|---|---|---|---|---|---|---|---|---|---|
| | | | | Clinical data of Family 1 patients | | | | | | |
| | G[1] | Age (Yrs) | Onset[2] | Seizure type | T[3] | P[4] | SEP[5] | C[6] | AEDs | Cure[7] |
| II1 | M | D[8] | 58 | GTC | + | NA | NA | NA | PHT | No seizure |
| III3 | F | 59 | 40 | M[9] + GTC | + | NA | 38.0 | + | PHT | No seizure |
| III7 | F | 52 | 38 | M + GTC | + | NA | 75.5 | + | PB and PHT | No seizure |
| III9 | M | 49 | 30 | M + GTC | + | NA | 19.04 | + | PB and PHT | No seizure |
| IV6 | F | 36 | 35 | M + GTC | − | NA | 22.28 | + | PHT | No seizure |
| IV11 | M | 24 | 11 | M + GTC | + | NA | 11.97 | + | VPA | No seizure |

[1]G: Gender
[2]Age of patient in years at time of disease onset.
[3]T: tremor
[4]P: Polycystic kidney/polycystic liver
[5]SEP: Upper limb SEP (P25-N 30), in μV.
[6]C: C reflex
[7]Cure: AED Curative effect.
[8]D: Deceased
[9]M: Myoclonus Preparation of the genetically-modified rat in knock-in mode using a PKHD1L1 gene (Gene ID: 314917, Pkhd1l1-201 transcript ENSRNOT00000005958.7, NM_001034931):

1. Cas9/sgRNA Design and Construction 1.1 Cas9/sgRNA Design

Based on sgRNA design principles, 7 sgRNAs were designed in the 5' target site and 3' target site area, respectively (Table 2).

1.2 Construction of Cas9/sgRNA Plasmid

Figure 3:
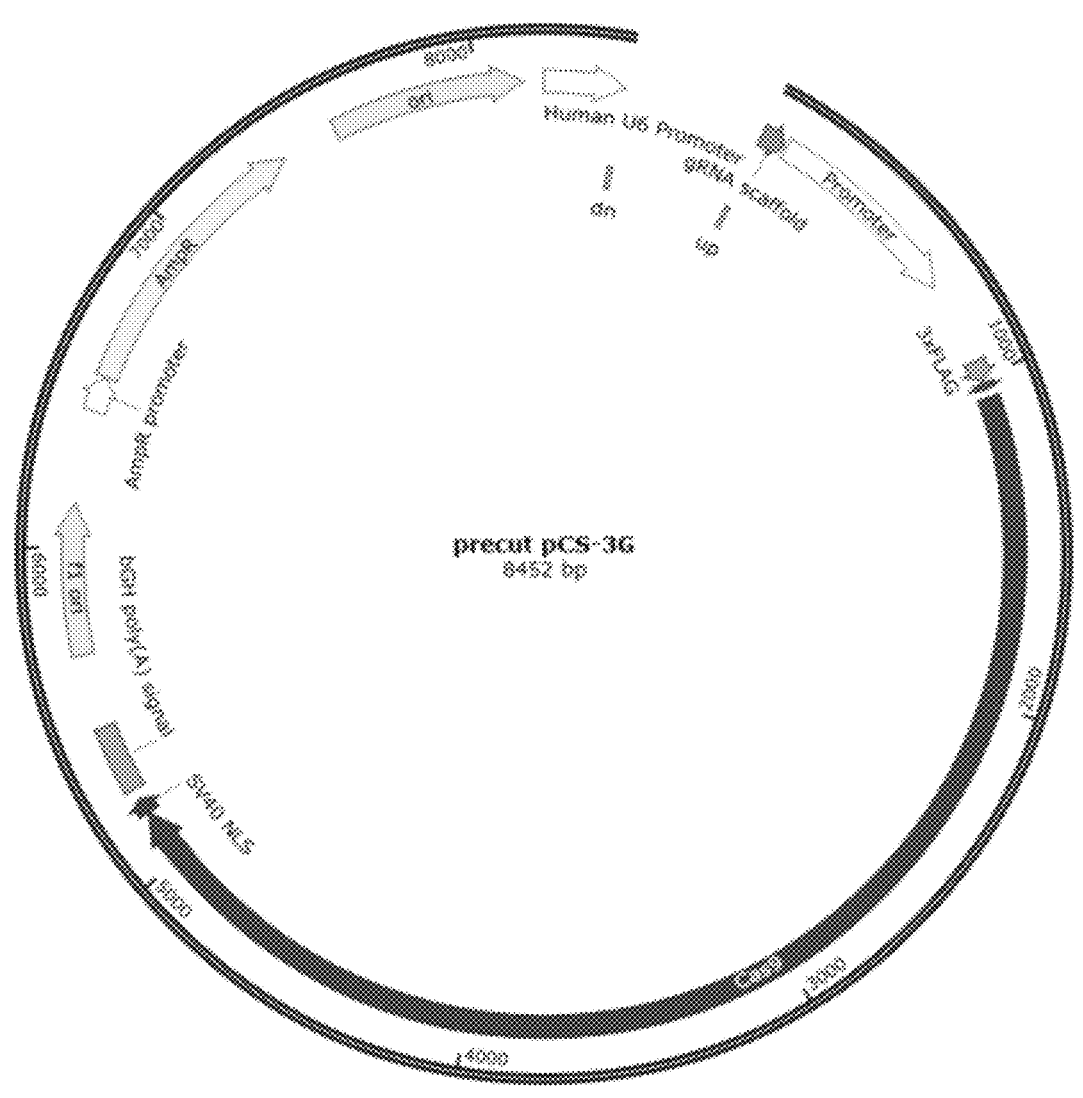
FIG. 3 shows the plasmid map of precut pCS-3G.

The sgRNA sequence synthesis primers shown in Table 1 were designed and connected to the pCS-3G carrier shown in FIG. 3 by annealing polymerization (65° C., 5 min). After the conversion of the connected product, the sample was sent for sequencing verification.

A CRISPR/Cas9 activity detection method (UCATM [Universal CRISPR Activity Assay]) was used to detect sgRNA activity, and the results are shown in FIGS. 5A-B. PKHD1L1-sgRNA1 (Guide #1) and PKHD1L1-sgRNA12 (Guide #12) were selected to carry out the next experiment.

1.3 RNA Preparation of sgRNA

PKHD1L1-sgRNA1 and PKHD1L1-sgRNA12 were connected to plasmid vectors with a T7 promoter and transcribed in vitro to obtain RNA for microinjection (FIG. 6).

1.4 Construct the Targeting Vector Shown in FIG. 4.

1.5 Microinjection of Cas9/sgRNA

Cas9/sgRNA and the targeting vector were microinjected into fertilized rat eggs, and the rat eggs injected with the Cas9/sgRNA and the targeting vector were implanted into young female rats exhibiting false pregnancy. Data for the F0 rats at/after birth is shown in Table 6.

TABLE 6

| Birth statistics of $F_0$ rats | | | | | |
|---|---|---|---|---|---|
| Date | Family | Number of transferred zygotes | Due date | Number of births | Positive number |
| 2018 Jan. 12 | SD | 210 | 2018 Feb. 3 | 41 | 0 |
| 2018 Mar. 30 | SD | 250 | 2018 Apr. 21 | 35 | 2 |
| 2018 Apr. 8 | SD | 328 | 2018 Apr. 30 | 44 | 5 |

1.6 Genotype Detection of $F_0$ Generation Rats

Figure 8:
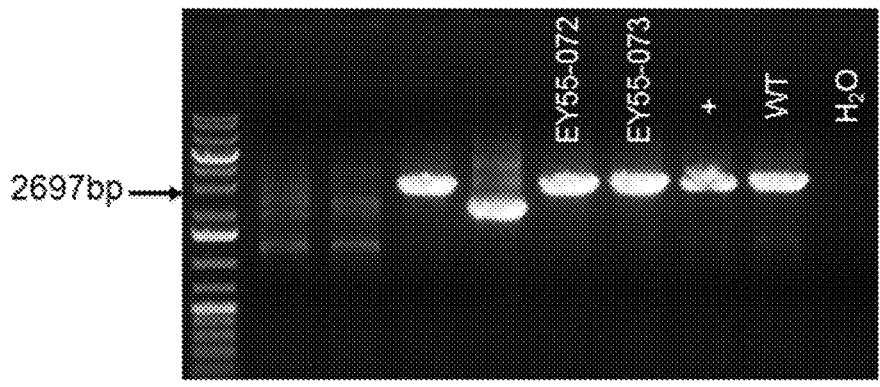
FIG. 8 is a reproduction of a Southern blot showing the results of $F_0$-generation identification by PCR using PKHD1L1-R-GT-F/PKHD1L1-R-GT-R in accordance with the present invention.

Primers PKHD1L1-L-GT-F/PKHD1L1-L-GT-R (Mut: 2662 bp, WT: 2650 bp) and PKHD1L1-R-GT-F/PKHD1L1-R-GT-R (Mut: 2697 bp, WT: 2680 bp) were identified by PCR, and the genotype of the $F_0$ generation rats was conventionally determined. The results are shown in FIGS. 7 and 8. The PCR products and sequencing showed that EY55-072 and EY55-073 are positive $F_0$ rats.

1.7 Genotypes and Southern Blot Identification of $F_1$ Generation Rats

An $F_0$ generation rat having a positive genotype were selected to mate with a wild-type rat to obtain $F_1$ generation rats with a stable positive genotype (e.g., for having or exhibiting a positive phenotype for epilepsy). The mating results are shown in Table 7.

TABLE 7

| Mating statistics | | | | |
|---|---|---|---|---|
| Rat OD | Mating date | Maturity date | Birth number | No. Positive |
| EY55-073 (♀) | 2018 May 24 | 2018 Jun. 14 | 24 | 10 |

Figure 9:
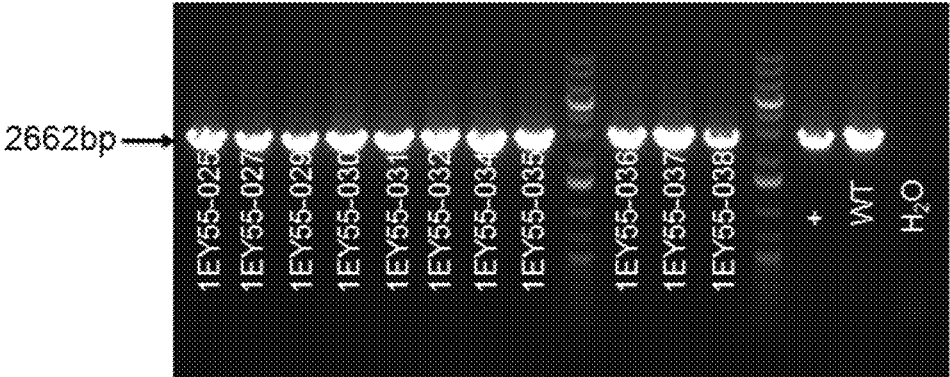
FIG. 9 is a reproduction of a Southern blot showing the results of $F_1$-generation identification by PCR using PKHD1L1-L-GT-F/PKHD1L1-L-GT-R in accordance with the present invention.
Figure 10:
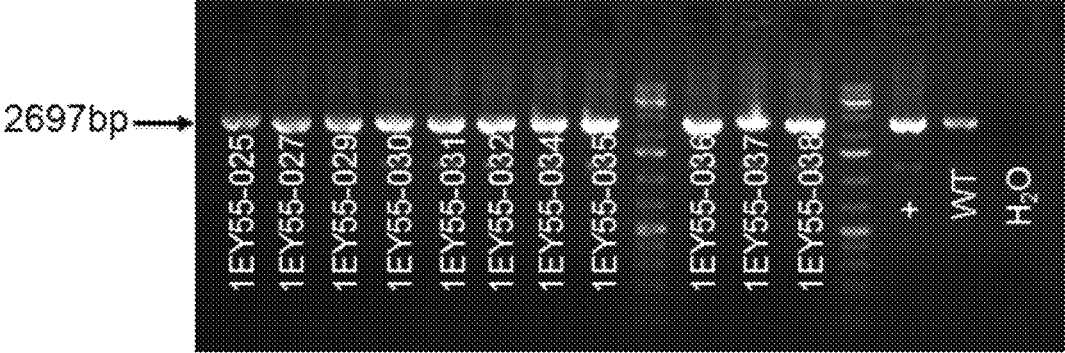
FIG. 10 is a reproduction of a Southern blot showing the results of $F_1$-generation identification by PCR using PKHD1L1-R-GT-F/PKHD1L1-R-GT-R in accordance with the present invention.

1.7.1 Genotype Identification of $F_1$ Generation:

The primers for identification of $F_1$ generation rats are the same and/or were designed according to the same procedure(s) as those in the method of genotype identification and/or detection in the $F_0$ generation. The results are shown in part in FIGS. 9 and 10. PCR identification and point mutation site sequencing are used to obtain the results. The results indicated that 1EY55-025, 1EY55-027, 1EY55-029, 1EY55-030, 1EY55-031, 1EY55-032, 1EY55-034, 1EY55-035, 1EY55-036, 1EY55-037 and 1EY55-038 were positive $F_1$ generation rats.

1.7.2 Southern Blot Analysis of $F_1$ Generation Positive Rats

Figure 11:
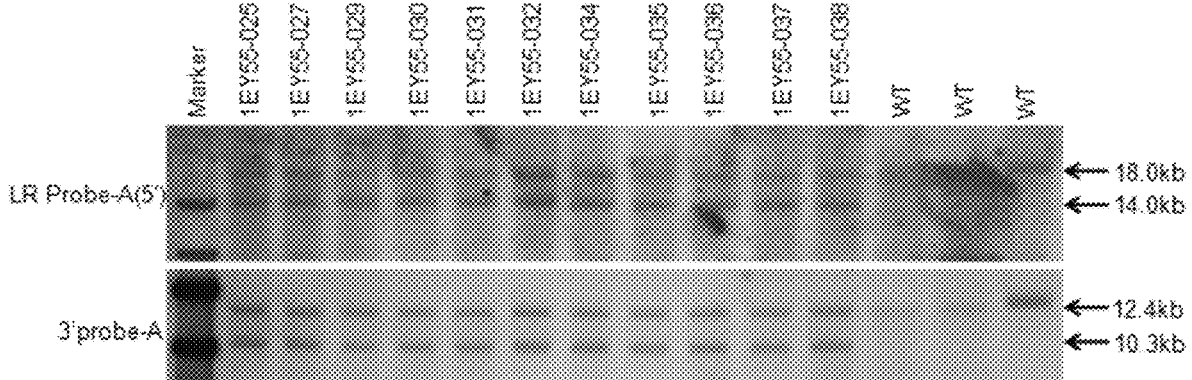
FIG. 11 is a reproduction of a Southern blot from an exemplary analysis of $F_1$-generation positive rats in accordance with the present invention.

The DNA of $F_1$ generation rats (e.g., obtained from the tail) identified as positive by PCR was extracted and tested by Southern blotting and sequencing. The test results are shown in FIG. 11, and show that 1EY55-025, 1EY55-027, 1EY55-029, 1EY55-030, 1EY55-031, 1EY55-032, 1EY55-034, 1EY55-036, 1EY55-037 and 1EY55-038 are correctly reassembled and do not have a random insertion.

1.7.3 Genotype Analysis

Figure 12:
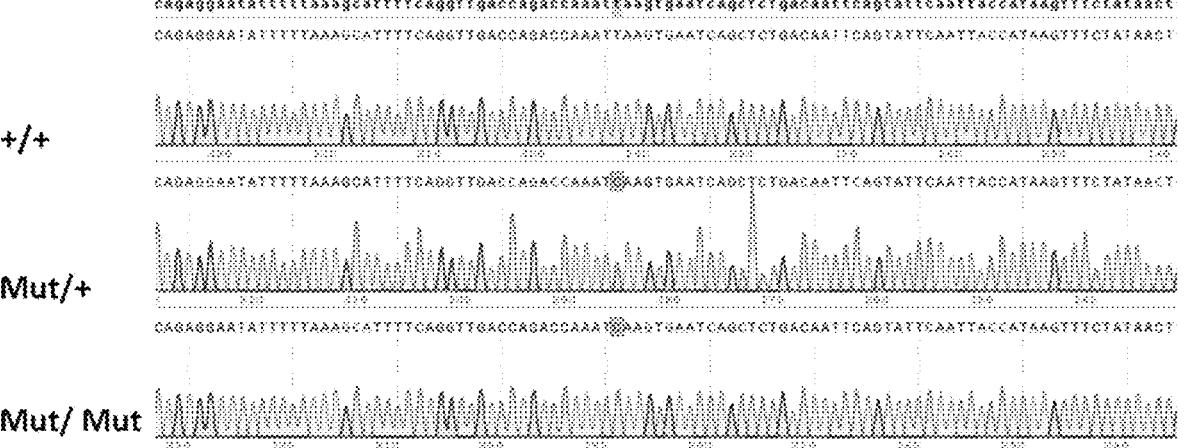
FIG. 12 shows an exemplary genotype sequencing analysis of wild-type, heterozygous and positive $F_1$ generation rats in accordance with the present invention.

Primers PKHD1L1-R-GT-F and PKHD1L1-L-GT-R were used for PCR validation and sequencing on positive $F_1$ generation young rats with correct recombination and no random insertions. The results are shown in FIG. 12, where "Mut/Mut" refers to a homozygous genotype, "Mut/+" refers to a heterozygous genotype, and "+/+" refers to a wild-type genotype.

Example 2

The epileptic behavior and phenotype(s) of rats having the PKHD1L1 gene with the point mutation constructed in Example 1 were analyzed.

Three male heterozygous rats having the PKHD1L1 gene with the point mutation (PKHD1L1+/−) were first observed for 5 consecutive days for spontaneous epilepsy. However, no spontaneous epileptic behavior was observed.

Figures 13A, 13B, 13C:
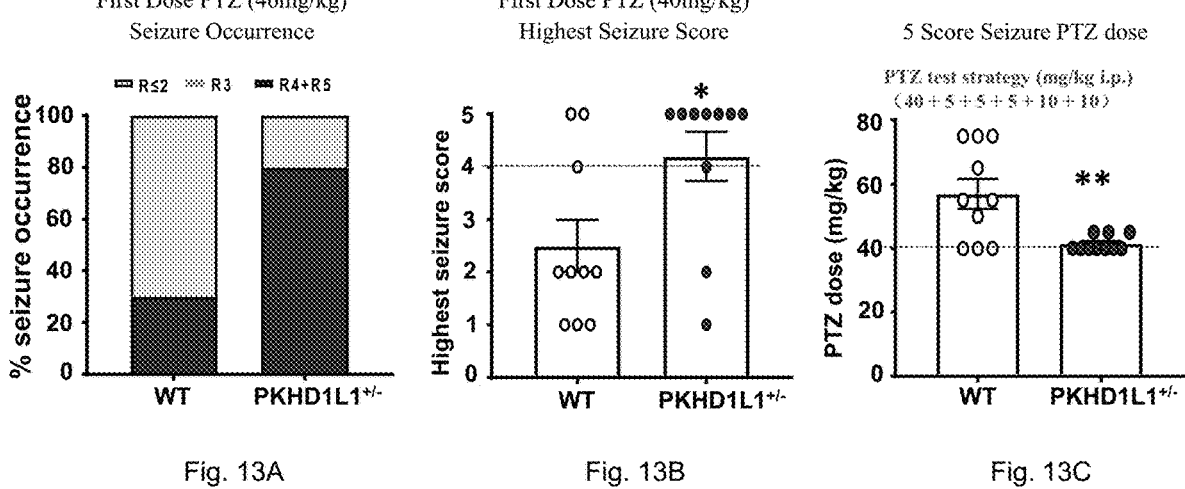
FIGS. 13A-C are graphs showing the results of epileptic susceptibility determinations in wild-type rats and PKHD1L1+/− rats in accordance with the present invention.
Figures 16A, 16B, 16C, 16D, 16E, 16F:
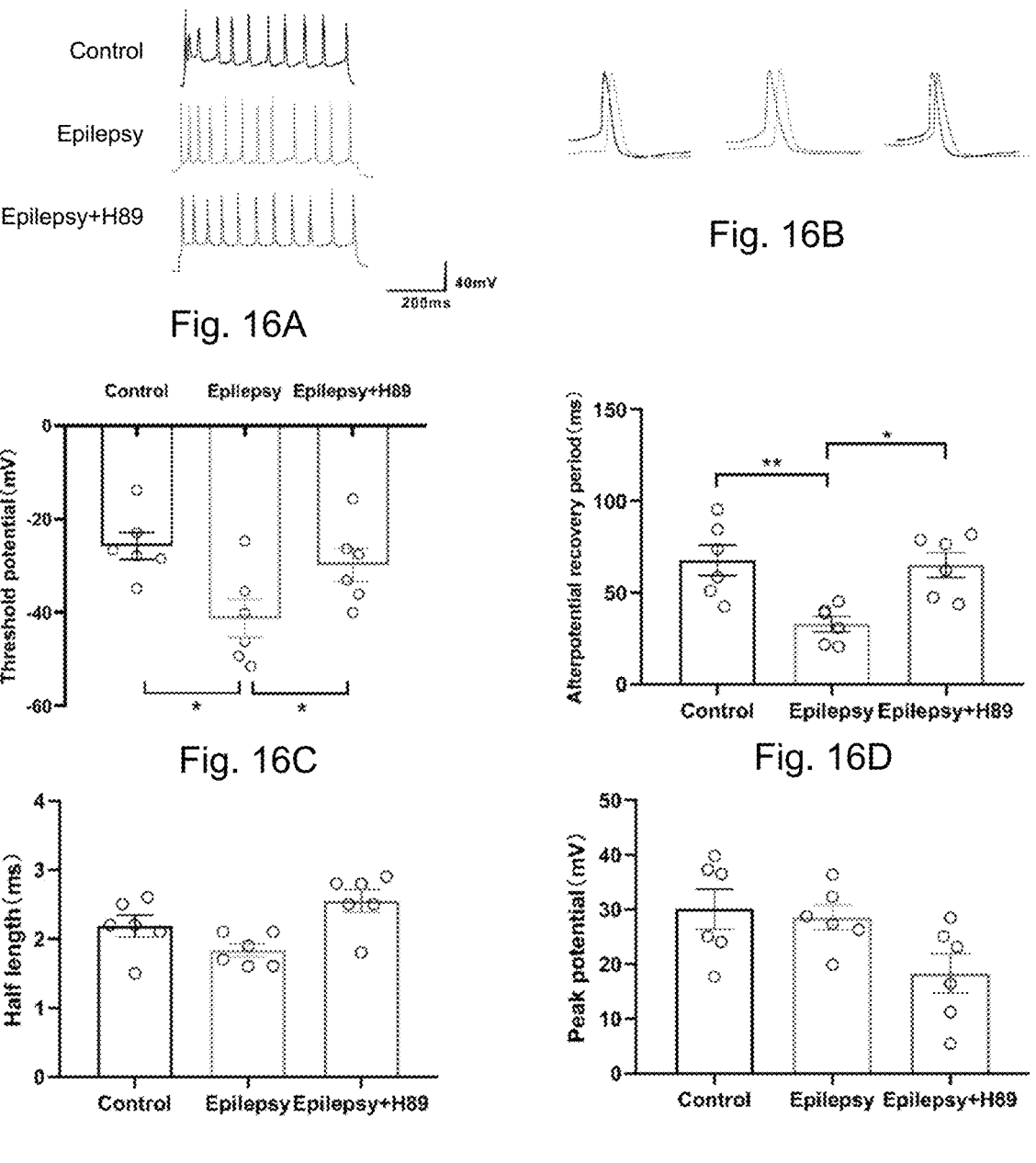
FIGS. 16A-F are waveforms (FIGS. 16A-B) and graphs (FIGS. 16C-F) showing the effect of H89 on the action potential of pyramidal neurons in the cerebral cortex of the control, epileptic and treated rats, wherein FIG. 16A are waveforms of the action potential of pyramidal neurons in the cerebral cortex of rats in each group, FIG. 16B are sample single action potentials of pyramidal neurons in each group of rats.

Subsequently, the epileptic susceptibility of PKHD1L1+/− rats was studied using a PTZ-induced epilepsy model: A total of 10 male PKHD1L1+/− rats and 10 male wild-type (WT) rats with body weights matched with age (in weeks) were selected for inducing epileptic seizures with PTZ (40 mg/kg). The dose of PTZ selected is lower than the conventional dose in such animal modeling. Only 2 out of the 10 wild-type rats (20%), but 7 out of the 10 (70%) PKHD1L1+/− rats, were induced to have grand mal seizures of grade 4-5 (see FIG. 13A). The maximum seizure level reached by the PKHD1L1+/− rats was significantly higher than that of the wild-type rats (see FIG. 13B). Further, additional PTZ injections (5 mg/kg at 15-minute intervals) were administered in rats that did not reach grade 4-5. The mean dose of PTZ required for wild-type rats to exhibit such seizures was statistically significantly higher than that required for PKHD1L1+/− rats (see FIG. 13C). These results indicate that PKHD1L1+/− rats having a PKHD1L1 gene with the c.2602A>T point mutation have seizure susceptibility characteristics.

The PKHD1L1+/− rats were further tested by SEP to detect a phenotype corresponding to abnormal cortical excitability. The specific methods are as follows.

The head and limbs of PKHD1L1+/− rats were fixed in a prone position, and the posterior tibialis nerve of the ankle of the right hind limb was stimulated by electrocutaneous stimulation. The stimulation parameters included a constant pressure square wave having a wave or pulse width of 0.1 ms and a frequency of 3 Hz. The intensity of the stimulation was regulated and/or adjusted to cause posterior toe micromovement. A subcutaneous needle on the back was grounded. The recording needle/electrode was inserted subcutaneously into the Cz region at the top of the skull, and the reference needle/electrode was inserted subcutaneously above the nose. The signal extracted from the recording needle/electrode was filtered and amplified, and input into a computer for determining an average superposition of 1024 superposition times, using an analysis time of 56 ms. The resulting somosensory evoked potential pattern was displayed and printed to measure its peak latency. Waves are labelled according to their polarity and order of occurrence (P1, P2, . . . . N1, N2, where P is a positive wave and N is a negative wave). The number indicates the number of the wave in the order in which the waves appear.

The results are shown in Table 8. Compared with wild-type (WT) rats with matched body weight, PKHD1L1+/− (MU) rats had a significantly shorter incubation period of SEP (10.17±1.17, vs. 12.32±1.65, P=0.0071), and the amplitude of SEP tended to increase (3.95±1.72, vs. 2.87±1.6, P=0.1794), indicating that the cortical excitability of PKHD1L1+/− rats was significantly higher than that of wild-type rats. This study further verified the increased cortical excitability of PKHD1L1+/− rats, which better simulate the phenotype of FAME patients and other epilepsy patients.

TABLE 8

Latency and amplitude of SEP in WT and MU rats

| No. | Gender | Weight (g) | Group | P40-N50 Wave amplitude (μV) | P40 Latency (ms) |
|---|---|---|---|---|---|
| 20230304001 | M | 244 | WT | 1.76 | 13.6 |
| 20230304002 | F | 226 | WT | 2.4 | 10.5 |
| 20230304003 | F | 273 | WT | 4 | 10.4 |
| 20230304004 | F | 261 | WT | 5.4 | 10.9 |
| 20230304005 | M | 428 | WT | 3.3 | 13.8 |
| 20230317006 | F | 308 | WT | 4.2 | 14 |
| 20230317007 | M | 475 | WT | 2.2 | 13.9 |
| 20230317008 | M | 477 | WT | 2.1 | 13.5 |
| 20230317009 | M | 480 | WT | 3.2 | 14.8 |
| 20230317010 | M | 487 | MU | 6.8 | 10 |
| 20230330011 | M | 385 | WT | 5.6 | 11.5 |
| 20230330012 | F | 365 | WT | 0.3 | 11.7 |
| 20230330013 | M | 586 | MU | 1.92 | 10.9 |
| 20230330014 | M | 572 | MU | 4 | 9.7 |
| 20230330015 | M | 608 | MU | 2.1 | 12.5 |
| 20230403016 | F | 342 | MU | 3.4 | 9.5 |
| 20230403017 | F | 320 | MU | 5.3 | 9.1 |
| 20230403018 | F | 315 | MU | 4.1 | 9.5 |
| 20230428019 | F | 403.9 | WT | 1.8 | 10.1 |
| 20230428020 | M | 495.8 | WT | 1.05 | 11.4 |

Example 3

Results of Electrophysiological Examination of Transgenic Animal Brain Slices

In transgenic animals (PKHD1L1+/− rats), neuronal excitability increased, and H89 reduced the frequency of spontaneous excitatory post synaptic currents (sEPSC) in pyramidal neurons in the cerebral cortex.

A patch clamp technique was used to record sEPSC and sIPSC (e.g., spontaneous inhibitory post synaptic currents) of cortical pyramidal neurons in the computer, and to observe the changes in excitatory synaptic transmission and inhibitory synaptic transmission of pyramidal neurons in each group of rats, so as to reflect any changes in neuronal excitability. It was found that the sEPSC amplitude and frequency were higher in the epilepsy group (e.g., the PKHD1L1+/− rats) than in the control group (e.g., the wild-type rats), and the amplitude and frequency (e.g., in sEPSC) decreased after H89 treatment. Experimental results also showed that excitability was increased in the epileptic group (e.g., the PKHD1L1+/− rats), and H89 could be used to reduce the amplitude and frequency of cortical sEPSC and reduce its excitability (e.g., in the PKHD1L1+/− rats), thus playing a therapeutic role (see FIGS. 14A-F).

H89 does not affect the excitability of pyramidal neurons (and optionally affect Na+ and K+ currents) in the cerebral cortex. Neuronal excitability is related to Na+ and K+ currents, so the Na+ and K+ currents in pyramidal neurons in the cerebral cortex of each group of rats (e.g., PKHD1L1+/− and wild-type) were recorded. As shown in FIGS. 15A-B, there was no difference in Na+ and K+ currents in pyramidal neurons of rats among all groups (3 young rats in each group, 6 cells in the control [WT] group, 6 cells in the epilepsy [e.g., PKHD1L1+/−] group, and 6 cells in the epilepsy+H89 group), P<0.05.

H89 can reduce the excitability of pyramidal neurons in the cerebral cortex of rats with epilepsy. In order to further confirm the excitability of pyramidal neurons in the cerebral cortex, the action potential of pyramidal neurons was recorded. Action potential can intuitively reflect the excitability of neurons. The recorded action potentials of pyramidal neurons showed that the action potential threshold of rats in the epilepsy group (e.g., PKHD1L1+/− rats) decreased (P<0.05), but the action potential threshold increased after H89 treatment (P<0.05). Compared with the control group (e.g., WT rats), the positive potential of the epileptic group was decreased after H89 treatment, and the neuronal potential was increased after H89 treatment (P>0.05). There was no difference in the peak and half-duration of the action potential between the two groups. A decrease in positive post-potential of pyramidal neurons in epileptic rats indicated that the function of the sodium ion pump was weakened. It was shown that a reduced neuron action potential threshold in epileptic rats indicates decreased excitability of pyramidal neurons, and H89 reversed this trend and improved epileptic symptoms in rats (FIGS. 16A-F).

Although the above embodiments give a detailed description of the invention, they are only part of the embodiments of the invention, not all embodiments, and other embodiments can be obtained according to the embodiments without creativity, which are within the scope of protection of the invention.

What is claimed is:

1. A method for constructing a rat model with a PKHD1L1 gene point mutation, comprising:

obtaining a single-guide RNA (sgRNA) having the full-length sequence of SEQ ID NO: 5 and the full-length sequence of SEQ ID NO: 6, ligating the sgRNA into a plasmid vector with an operably linked T7 promoter, transcribing the plasmid vector in vitro to obtain a Cas9 in complex with the sgRNA), injecting the Cas9 in complex with the sgRNA and a targeting vector having the full-length nucleotide sequence of SEQ ID NO: 27 into fertilized rat eggs to obtain gene-edited fertilized eggs, and placing the gene-edited fertilized eggs in a uterus of pseudopregnant young rats to obtain F0 generation chimeric rats having a PKHD1L1 L867S mutation.

2. The method of claim 1, wherein the plasmid vector is a pCS-3G vector.

3. The method of claim 2, wherein the sgRNA is ligated into the pCS-3G vector by annealing polymerization to form a connected product, and the connected product is transcribed in vitro to obtain the Cas9 in complex with the sgRNA.

4. The method of claim 1, further comprising, after obtaining the F0 generation chimeric rats, identifying the rats having the PKHD1L1 L867S gene point mutation by PCR, wherein when using SEQ ID NO: 7 and SEQ ID NO:

8 for PCR identification, amplifying a 2662 bp sequence identifies the F0 generation chimeric rats having the PKHD1L1 L867S gene point mutation, and when using SEQ ID NO: 9 and SEQ ID NO: 10 for PCR identification, amplifying a 2697 bp sequence identifies the F0 generation chimeric rats having the PKHD1L1 L867S gene point mutation.

5. The method of claim 4, wherein the PCR includes pre-denaturing at 94° C. for 2 min; denaturing at 98° C. for 10 s, annealing at 67° C. for 30 s, extending at 68° C. at 1 kb/min, 15 cycles, annealing at a temperature of −0.7° C. per cycle; denaturing at 98° C. for 10 s, annealing at 57° C. for 30 s, extending at 68° C. at 1 kb/min, 25 cycles; and extending at 68° C. for 10 min.

6. A method for constructing a stable genetic PKHD1L1 gene point mutation rat model, comprising mating the $F_0$ generation chimeric rat having the PKHD1L1 L867S gene point mutation obtained by the method of claim 1 with wild-type rats, wherein the stable genetic PKHD1L1 gene point mutation rat model is a heterozygote.

7. The method of claim 6, further including identifying the heterozygote of the $F_1$ generation by genotype identification.

8. The method of claim 7, wherein the genotype identification includes PCR identification, Southern blot identification, or sequencing identification.

* * * * *

SEQUENCE LISTING

```
Sequence total quantity: 27
SEQ ID NO: 1          moltype = DNA  length = 45
FEATURE               Location/Qualifiers
source                1..45
                      mol_type = other DNA
```

-continued

```
                           organism = synthetic construct
SEQUENCE: 1
gcatcaagct tggtaccgat aatcacaaga cacaatagac gcaga                            45

SEQ ID NO: 2        moltype = DNA   length = 45
FEATURE             Location/Qualifiers
source              1..45
                    mol_type = other DNA
                    organism = synthetic construct
SEQUENCE: 2
acttaatcgt ggaggatgat cttgcttcac aaacaaaggg acctg                            45

SEQ ID NO: 3        moltype = DNA   length = 45
FEATURE             Location/Qualifiers
source              1..45
                    mol_type = other DNA
                    organism = synthetic construct
SEQUENCE: 3
gcatcaagct tggtaccgat gacagaagca aagccagaga ataaa                            45

SEQ ID NO: 4        moltype = DNA   length = 46
FEATURE             Location/Qualifiers
source              1..46
                    mol_type = other DNA
                    organism = synthetic construct
SEQUENCE: 4
acttaatcgt ggaggatgat gaagtttaca taactcaagc agtcca                           46

SEQ ID NO: 5        moltype = DNA   length = 17
FEATURE             Location/Qualifiers
source              1..17
                    mol_type = other DNA
                    organism = synthetic construct
SEQUENCE: 5
ggtaggctag actttaa                                                           17

SEQ ID NO: 6        moltype = DNA   length = 18
FEATURE             Location/Qualifiers
source              1..18
                    mol_type = other DNA
                    organism = synthetic construct
SEQUENCE: 6
ggaaagttga gtgttcca                                                          18

SEQ ID NO: 7        moltype = DNA   length = 27
FEATURE             Location/Qualifiers
source              1..27
                    mol_type = other DNA
                    organism = synthetic construct
SEQUENCE: 7
tgcagatgtt gtgagaaaag caagaca                                                27

SEQ ID NO: 8        moltype = DNA   length = 30
FEATURE             Location/Qualifiers
source              1..30
                    mol_type = other DNA
                    organism = synthetic construct
SEQUENCE: 8
ccagtcttga tgttttatag atacttcccc                                             30

SEQ ID NO: 9        moltype = DNA   length = 27
FEATURE             Location/Qualifiers
source              1..27
                    mol_type = other DNA
                    organism = synthetic construct
SEQUENCE: 9
tccaatccat ttatgtggat gccgtgt                                                27

SEQ ID NO: 10       moltype = DNA   length = 28
FEATURE             Location/Qualifiers
source              1..28
                    mol_type = other DNA
                    organism = synthetic construct
SEQUENCE: 10
aggatgcttg aatctttctt ctaagggg                                               28

SEQ ID NO: 11       moltype = DNA   length = 19
FEATURE             Location/Qualifiers
source              1..19
```

-continued

```
                              mol_type = other DNA
                              organism = synthetic construct
SEQUENCE: 11
ggccttcgta ttagctata                                           19

SEQ ID NO: 12          moltype = DNA  length = 22
FEATURE                Location/Qualifiers
source                 1..22
                       mol_type = other DNA
                       organism = synthetic construct
SEQUENCE: 12
ggaatcccta tagctaatac ga                                       22

SEQ ID NO: 13          moltype = DNA  length = 19
FEATURE                Location/Qualifiers
source                 1..19
                       mol_type = other DNA
                       organism = synthetic construct
SEQUENCE: 13
ggctactatg ttaaatatg                                           19

SEQ ID NO: 14          moltype = DNA  length = 18
FEATURE                Location/Qualifiers
source                 1..18
                       mol_type = other DNA
                       organism = synthetic construct
SEQUENCE: 14
ggagtcttaa agtgaacc                                            18

SEQ ID NO: 15          moltype = DNA  length = 20
FEATURE                Location/Qualifiers
source                 1..20
                       mol_type = other DNA
                       organism = synthetic construct
SEQUENCE: 15
gggaagttaa gaaacacaat                                          20

SEQ ID NO: 16          moltype = DNA  length = 22
FEATURE                Location/Qualifiers
source                 1..22
                       mol_type = other DNA
                       organism = synthetic construct
SEQUENCE: 16
ggcacctgtg ggcatgtgta ga                                       22

SEQ ID NO: 17          moltype = DNA  length = 22
FEATURE                Location/Qualifiers
source                 1..22
                       mol_type = other DNA
                       organism = synthetic construct
SEQUENCE: 17
ggtcaccctt aagcccccaa aa                                       22

SEQ ID NO: 18          moltype = DNA  length = 22
FEATURE                Location/Qualifiers
source                 1..22
                       mol_type = other DNA
                       organism = synthetic construct
SEQUENCE: 18
ggtctacatg tatgtcacca cc                                       22

SEQ ID NO: 19          moltype = DNA  length = 20
FEATURE                Location/Qualifiers
source                 1..20
                       mol_type = other DNA
                       organism = synthetic construct
SEQUENCE: 19
ggttaattta gtcatgtata                                          20

SEQ ID NO: 20          moltype = DNA  length = 20
FEATURE                Location/Qualifiers
source                 1..20
                       mol_type = other DNA
                       organism = synthetic construct
SEQUENCE: 20
ggtcaaataa ctagaactgc                                          20

SEQ ID NO: 21          moltype = DNA  length = 19
FEATURE                Location/Qualifiers
```

-continued

```
source                  1..19
                        mol_type = other DNA
                        organism = synthetic construct
SEQUENCE: 21
ggaagttatt tgttatgaa                                                         19

SEQ ID NO: 22           moltype = DNA   length = 20
FEATURE                 Location/Qualifiers
source                  1..20
                        mol_type = other DNA
                        organism = synthetic construct
SEQUENCE: 22
ggaaatctgg gtccttagaa                                                        20

SEQ ID NO: 23           moltype = DNA   length = 24
FEATURE                 Location/Qualifiers
source                  1..24
                        mol_type = other DNA
                        organism = synthetic construct
SEQUENCE: 23
aggatctctg gccaacttca ttgg                                                   24

SEQ ID NO: 24           moltype = DNA   length = 27
FEATURE                 Location/Qualifiers
source                  1..27
                        mol_type = other DNA
                        organism = synthetic construct
SEQUENCE: 24
ttctgtttct aatgttagtg gaaatgc                                                27

SEQ ID NO: 25           moltype = DNA   length = 25
FEATURE                 Location/Qualifiers
source                  1..25
                        mol_type = other DNA
                        organism = synthetic construct
SEQUENCE: 25
ccagtcccca gaacaattgg ctaga                                                  25

SEQ ID NO: 26           moltype = DNA   length = 25
FEATURE                 Location/Qualifiers
source                  1..25
                        mol_type = other DNA
                        organism = synthetic construct
SEQUENCE: 26
actgtgtgga ggcaaagaag catga                                                  25

SEQ ID NO: 27           moltype = DNA   length = 7320
FEATURE                 Location/Qualifiers
source                  1..7320
                        mol_type = other DNA
                        organism = synthetic construct
SEQUENCE: 27
tcgcgcgttt cggtgatgac ggtgaaaacc tctgacacat gcagctcccg gagacggtca    60
cagcttgtct gtaagcggat gccgggagca gacaagcccg tcaggggcgcg tcagcggggtg   120
ttggcgggtg tcggggctgg cttaactatg cggcatcaga gcagattgta ctgagagtgc   180
accatatgcg gtgtgaaata ccgcacagat gcgtaaggag aaaataccgc atcaggcgcc   240
attcgccatt caggctgcgc aactgttggg aagggcgatc ggtgcgggcc tcttcgctat   300
tacgccagct ggcgaaaggg ggatgtgctg caaggcgatt aagttgggta acgccagggt   360
tttcccagtc acgacgttgt aaaacgacgg ccagtgaatt cgagctcggt acctcgcgaa   420
tgcatctaga tccgacgctt taggagtgaa taccgcagaa gacggccgag acagatgcat   480
tctgtggccg ttactccctg aaaaacccag ctgttctttt tgactcaaca gatgtcaagc   540
caaacaaatt accatatgga gacattttat tatttcctta taatcaggtg agattgtgaa   600
aactgtatgc taattgaatc tgggaaatac ccagctaata taatttcatg aaaatttaag   660
actaagaaaa ggacttgcca ttttgaatca tgtcatgttg gacaggagta atgattcata   720
ttctggtttc cgtggtctct ctccaggtga ttctcagaag aaaagagaag gacgaggagg   780
aaggaggggag agagcaatag caataaggaa atatattgtc atgtcttatg ctttattta   840
ttattttata agacatgtta ttcataaatt ttaattggaa tttatagatc gctaactctc   900
ataggggtgta aaatatcttc tattttaaaa ggaaatagca tccaaatata caaattcact   960
gttaagtctt gtcttctgta agaggaagtt cccaattccc tgacagctga ttagtcaaaa  1020
tctactggtt tattttgttt ttaaagctct tttatattct atataaaatg ttcaataagt  1080
atatagtgat ttgtattgta ttactttgaa ttgttataat acaaagtaat tgtaaaaatg  1140
ttgttattga ctcctttcat atattttatg tagctgtgtt tagcatacaa aggatctctg  1200
gccaacttca ttggtctgaa gttcaagtat gaagacagtg gcaagatcat tagaagtgct  1260
gatatgcaat ttgaatataa ctttgcttct ggaaataagt aagatacatt atgggttcaa  1320
aacaagttat agtacaacat acatgctgta gagatggtct catttctttt gctcagcatg  1380
accaggttgg cttcctttca gagttacagg aacaactcaa cacatgcaaa tcagtaaaca  1440
tgatgcagca catgataaag aacagaaatc acaagacaca atagacacag aaaagacttt  1500
tgacaaaatc caaaatctct tcacgataaa actcccaaag agactagtac tagaaggaat  1560
aagtctcgaa ttaataaagg atatatatga caagtttata ggcaacatta tatattaaaa  1620
```

-continued

```
agaaaaactg aaagcatttc cactaacatt agaaacagaa ttttatcct atttccaca    1680
tatttaacat agtagctaat tctatgctaa cttgttttca ctaatgtgat ctataccaat    1740
tgtgtttctt aacttcccac atatcttgat agaaagttat tttaaatccc tatagctaat    1800
acgaaggcta caaatataatc tgtttatgta cacaacacta atctgtcact gaatgaaatt    1860
ttttgtttta taaaatttgg gaagtgccat ttgttcgtgt ttgtgtgtac atacacctgt    1920
gggcatgtgt agaaggggtgt gtccatatgt aaacaagaga ggttaacatt gaacacttc    1980
cttagtcact ttccttgtta tttttgaggt ggagtcttaa agtgaacctg aagttcacca    2040
ggtaggctag acttgatatc aggccttaaa ggcaacgaac tccagagctg ctcctgtttc    2100
tgctctccag ttctgtcacc aaagactgtg gtaccagtgt tttacaagga tgttgggagc    2160
ttaaactcag gtccctttgt ttgtgaagca agtattttcc aaatagagcc atctctctaa    2220
cccactgttc tttaaattat aacacctttt agaatgtgtg tgtgtgtgtt acaaatatga    2280
acactaaatt attcaatgta tttcagatgg acctacactt gcatagatct tctagatttc    2340
ttacaaacca aatatgctgg gacaagtttt tctctacaaa gaattagctt acaaaagtca    2400
tcagaattcc aatccattta tgtggatgcc gtgtacattg gacagatacc tacagtctca    2460
gtcttggatg gtatgttgag tcattttata tagactgata atgttacaaa tgaaagtttt    2520
attttagtgt cttagcatca tttattttatc atgtttgaat cacagattct gacaataaca    2580
gagcaaaaac ttaacaccat aatcttattt cccacttact tttttcagaa atgccaaagc    2640
gaagacctcc agcattagca aacagaggaa tattttaaa gcattttcag gttgaccaga    2700
ccaaatcaag tgaatcagct ctgacaattc agtattcaat taccataagt ttctataact    2760
gcagtcataa tataccaatg atgggtgtga gctttgggca ggtaagccta gaactttatg    2820
gtacaacttt aaactttgtg accatcagat ttgatgtagt gtatcttctt aactaaaaat    2880
atctggtgta caattgaata ttatatatta ttctgaaaca ggtcatga tttagagact    2940
tattgaggtt gaagatgaaa attttgaaaa ttcctcaaaa acttatctaa ggagaaaaac    3000
cagggggaagt atctataaaa catcaagact ggaggcttat gatatgactc agtgtgtaag    3060
catggtggct gttgccagtc ttgatagcct gagtataatt actgaaaacc gtataataga    3120
gacagccaag tcgtgcaagg tgtacctcat gacacatggt gacacacac aagcacacac    3180
acacacacac acacacacac acacacacac acacacacag gagagagaga gagacagaga    3240
gacagagaca gagacagaag caaagccaga gaataaatta aatgtaataa aaaggaagag    3300
tgtttgttgt cagatttaag tagaatttc cttatgtaca taaacattca ttggctctcc    3360
attttagaaa ttcatttaa agtatgtttt aggttaattt agtcatgtat atgggctttt    3420
tgcctgcatg tatatctaca tgtatgtcac cacctgggtc acagccagaa gagggtgtca    3480
aataactaga actgcaggaa aaaatgaccg tgagctgctt tgtaggtgct gggaattaaa    3540
tctgggtcct tagaagggca gccagtgttc ttcacccta agcccccaaa agggaatctt    3600
aaatatatat tattaaagga aagttgagtg ttactagtcc tcactcaggc caggqtttta    3660
aagtgttcta gaaattattt gttatgaacg gtatttcatt tgctcccatc aaaatctata    3720
ataagaaaga agatgtggtt ttccatggat ccaaaggaat tttaaaagtt catggactgc    3780
ttgagttatg taaacttcaa ccagaattca aagctaaaaa tgaacatttt aaaatgtaat    3840
ttcctataaa tacatacata ctttattagt tttatttcca caacaaatta aaaacaaata    3900
taggaaagct caagattaaa gtttaattaa cctagaaaga aactctcacc aaataaacac    3960
tttataactg aagatttgga agaagtaaat attctacaaa attttgtctt tacgtcattc    4020
tggagcagtg tttagtctta ctgtcttcaa gatggtcatt ttgttaatat gtcttgtaaa    4080
tgctttacta aataatagta aaaatgtgcc aagttgggat tttgtgttct tcaaatgcaa    4140
gcctttgcca agtttcctca tttacaccaa taactgctaa ttgcaatata gcttagtta    4200
tttaagatta aattggagaa tatggacctt gttttgtttt aaaaaaaaca tatccacatg    4260
taagatttc ttagttaggg ttttactgct gtgaacagac accatgacca aggcaactct    4320
tataaggaca acatttaatt ggggctggct tacacgttca gaggttcagt ccattattat    4380
catcaatgag ggagcatggc agcatccagg caggcatggt gtaggaggag ctgagttcta    4440
catcttgtac caaagtcgaa caggagaaga ctggcttcca ggaagctaag atgagggtca    4500
tgaagcctac tcccacagtg gcacaccaag gccacagccc caaatagtgc cactccctca    4560
gccaaacatc ttcaaaccat cacaaagacc aatacagcaa cacacagtat tttagaaact    4620
ttaactttga gattatttaa agaccaaacc caattgtaaa aaattattta gacatgacct    4680
catatccctc aggcattctt tccagcaaca agtgaaatag ccagattcca tacaaggttt    4740
ccagcatttg gtgttcttat catttttta tttaagcatt agaatagatg acattaatct    4800
cattaggatt taatttatat tttctaatgg ctggtgatgt tgaatatcat tttatgaact    4860
tctttactac ttatgtattt tctatggagt acttatttat gcttttttgaa cattttgaaa    4920
actttttaaa attcactta catcttactc actgacagcc tctcagtcac tccttcccca    4980
cagcatttct tccaccctct tcctcttctc tgagagggcc gacgctttag gagtgaatac    5040
catcggatcc cgggccgtc gactgcagag gcctgcatgc aagcttggcg taatcatggt    5100
catagctgtt tcctgtgtga aattgttatc cgctcacaat tccacacaac atacgagccg    5160
gaagcataaa gtgtaaagcc tggggtgcct aatgagtgag ctaactcaca ttaattgcgt    5220
tgcgctcact gcccgctttc cagtcgggaa acctgtcgtg ccagctgcat taatgaatcg    5280
gccaacgcgc ggggagaggc ggtttgcgta ttgggcgctc ttccgcttcc tcgctcactg    5340
actcgctgcg ctcggtcgtt cggctgcggc gagcggtatc agctcactca aaggcggtaa    5400
tacggttatc cacagaatca gggggataacg caggaaagaa catgtgagca aaaggccagc    5460
aaaaggccag gaaccgtaaa aaggccgcgt tgctggcgtt tttccatagg ctccgccccc    5520
ctgacgagca tcacaaaaat cgacgctcaa gtcagaggtg gcgaaacccg acaggactat    5580
aaagatacca ggcgtttccc cctggaagct ccctcgtgcg ctctcctgtt ccgaccctgc    5640
cgcttaccgg atacctgtcc gcctttctcc cttcgggaag cgtggcgctt tctcatagct    5700
cacgctgtag gtatctcagt tcggtgtagg tcgttcgctc caagctgggc tgtgtgcacg    5760
aaccccccgt tcagcccgac cgctgcgcct tatccggtaa ctatcgtctt gagtccaacc    5820
cggtaagaca cgacttatcg ccactggcag cagccactgg taacaggatt agcagagcga    5880
ggtatgtagg cggtgctaca gagttcttga agtggtggcc taactacggc tacactagaa    5940
gaacagtatt tggtatctgc gctctgctga agccagttac cttcggaaaa agagttggta    6000
gctcttgatc cggcaaacaa accaccgctg gtagcggtgg tttttttgtt tgcaagcagc    6060
agattacgcg cagaaaaaaa ggatctcaag aagatccttt gatcttttct acggggtctg    6120
acgctcagtg gaacgaaaac tcacgttaag ggattttggt catgagatta tcaaaaagga    6180
tcttcaccta gatccttta aattaaaaat gaagttttaa atcaatctaa agtatatatg    6240
agtaaacttg gtctgacagt taccaatgct taatcagtga ggcacctatc tcagcgatct    6300
gtctatttcg ttcatccata gttgcctgac tccccgtcgt gtagataact acgatacggg    6360
```

-continued

```
agggcttacc atctggcccc agtgctgcaa tgataccgcg agatccacgc tcaccggctc  6420
cagatttatc agcaataaac cagccagccg gaagggccga gcgcagaagt ggtcctgcaa  6480
ctttatccgc ctccatccag tctattaatt gttgccggga agctagagta agtagttcgc  6540
cagttaatag tttgcgcaac gttgttgcca ttgctacagg catcgtggtg tcacgctcgt  6600
cgtttggtat ggcttcattc agctccggtt cccaacgatc aaggcgagtt acatgatccc  6660
ccatgttgtg caaaaaagcg gttagctcct tcggtcctcc gatcgttgtc agaagtaagt  6720
tggccgcagt gttatcactc atggttatgg cagcactgca taattctctt actgtcatgc  6780
catccgtaag atgctttct gtgactggtg agtactcaac caagtcattc tgagaatagt  6840
gtatgcggcg accgagttgc tcttgcccgg cgtcaatacg ggataatacc gcgccacata  6900
gcagaacttt aaaagtgctc atcattggaa aacgttcttc ggggcgaaaa ctctcaagga  6960
tcttaccgct gttgagatcc agttcgatgt aacccactcg tgcacccaac tgatcttcag  7020
catcttttac tttcaccagc gtttctgggt gagcaaaaac aggaaggcaa aatgccgcaa  7080
aaaagggaat aagggcgaca cggaaatgtt gaatactcat actcttcctt tttcaatatt  7140
attgaagcat ttatcagggt tattgtctca tgagcggata catatttgaa tgtatttaga  7200
aaaataaaca aatagggggtt ccgcgcacat ttccccgaaa agtgccacct gacgtctaag  7260
aaaccattat tatcatgaca ttaacctata aaaataggcg tatcacgagg ccctttcgtc  7320
```